(12) United States Patent
Herron et al.

(10) Patent No.: US 7,163,938 B2
(45) Date of Patent: Jan. 16, 2007

(54) SUBSTITUTED CARBOXAMIDES

(75) Inventors: David Kent Herron, Indianapolis, IN (US); Sajan Joseph, Indianapolis, IN (US); Angela Lynn Marquart, Greenwood, IN (US); John Joseph Masters, Fishers, IN (US); David Mendel, Indianapolis, IN (US); Gerald Floyd Smith, Greenwood, IN (US); Philip Parker Waid, Indianapolis, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 136 days.

(21) Appl. No.: 10/415,756

(22) PCT Filed: Nov. 14, 2001

(86) PCT No.: PCT/US01/42941

§ 371 (c)(1),
(2), (4) Date: Apr. 30, 2003

(87) PCT Pub. No.: WO02/064567

PCT Pub. Date: Aug. 22, 2002

(65) Prior Publication Data

US 2004/0058959 A1    Mar. 25, 2004

Related U.S. Application Data

(60) Provisional application No. 60/253,501, filed on Nov. 28, 2000.

(51) Int. Cl.
  *A61P 7/00*     (2006.01)
  *A61K 31/44*    (2006.01)
  *A61K 31/55*    (2006.01)
  *C07D 213/00*   (2006.01)
  *C07D 401/12*   (2006.01)

(52) U.S. Cl. ...................................... 514/218; 540/575
(58) Field of Classification Search ................ 514/218; 540/575
   See application file for complete search history.

(56) References Cited

U.S. PATENT DOCUMENTS 6,140,351 A     10/2000  Arnaiz et al.
6,333,320 B1    12/2001  Koshio et al.
6,376,515 B1    4/2002   Zhu et al.
6,380,221 B1    4/2002   Arnaiz et al.
6,844,367 B1    1/2005   Zhu et al.
2002/0002183 A1 1/2002   Zhu et al.

FOREIGN PATENT DOCUMENTS

| AU | 2001 29827 A1 | 10/2001 |
|----|---------------|---------|
| EP | 1 057 818 A1  | 12/2000 |
| EP | 1 273 575 A1  | 1/2003  |
| JP | 2000 302765 A | 10/2000 |
| WO | WO 99/00121   | 1/1999  |
| WO | WO 99/00126   | 1/1999  |
| WO | WO 99/00127   | 1/1999  |
| WO | WO 99/00128   | 1/1999  |
| WO | WO 99/32447   | 7/1999  |
| WO | WO 00/39092   | 7/2000  |
| WO | WO 00/39111   | 7/2000  |
| WO | WO 00/39117   | 7/2000  |
| WO | WO 00/39118   | 7/2000  |
| WO | WO 01/19788   | 3/2001  |
| WO | WO 01/19798   | 3/2001  |
| WO | WO 01/64642   | 9/2001  |
| WO | WO 01/64643   | 9/2001  |
| WO | WO 01/74791   | 10/2001 |
| WO | WO 02/10154   | 2/2002  |
| WO | WO 02/14308   | 2/2002  |

OTHER PUBLICATIONS

Gresele et al., Novel Approaches to the Treatment of Thrombosis, TRENDS in Pharmacological Sciences, vol. 23, No. 1, pp. 25-32, Jan. 2002.*
Chemical Abstracts, vol. 71, No. 23, 1969 Columbus, Ohio, US; abstract No. 112967t, Yamamoto et al: "2, 3-diphenyl-4 (3H)-quinazolines" XP002207522 abstract & JP 06 916662 A (Sumitomo Chemical Co) Jul. 23, 1969.
Zentmyer, et al.: "The so-called acylanthranilis (3, 1, 4-benzoxazones). I. Preparation; reactions with water, ammonia and aniline; structure" Journal of Organic Chemistry, vol. 14, 1949, p. 967-981 Table IV entries 3-7.

* cited by examiner

*Primary Examiner*—Brenda Coleman
(74) *Attorney, Agent, or Firm*—Thomas E. Jackson

(57) ABSTRACT

This application relates to a compound of formula I (or a pharmaceutically acceptable salt thereof) as defined herein, pharmaceutical compositions thereof, and its use as an inhibitor of factor Xa, as well as a process for its preparation and intermediates therefor.

20 Claims, No Drawings

SUBSTITUTED CARBOXAMIDES

This application is the national stage of PCT/US01/42941, filed Nov. 14, 2001, and claims the benefit of U.S. Provisional Application No. 60/253,501, filed Nov. 28, 2000, which is incorporated by reference herein.

This invention relates to anticoagulant substituted carboxamides which demonstrate activity as inhibitors of factor Xa and, accordingly, which are useful antithrombotics in mammals. In particular it relates to substituted carboxamides having high anticoagulant activity, and antithrombotic activity. Thus, this invention relates to new substituted carboxamides which are inhibitors of factor Xa, pharmaceutical compositions containing the substituted carboxamides as active ingredients, and the use of the substituted carboxamides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the substituted carboxamides are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, B. Y. Zhu; R. M. Scarborough *Current Opinion in Cardiovascular, Pulmonary & Renal Investigational Drugs*, (1999), 1(1), 63–88, Recent Advances in Inhibitors of Factor Xa in the Prothrombinase Complex.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the substituted heterocyclic amides of the present invention, as defined below, are potent inhibitors of factor Xa which may have high bioavailability following oral administration.

According to the invention there is provided a compound of formula I

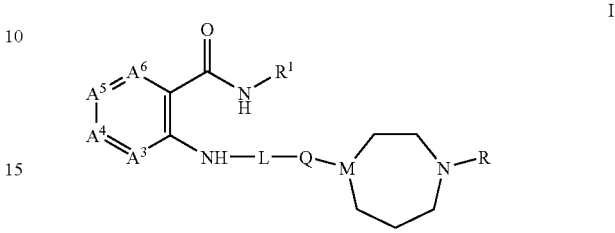

or a pharmaceutically acceptable salt thereof, wherein $R^1$ is 2-pyridinyl (which may bear a methyl, methoxy, methylthio, fluoro or chloro substituent at the 5-position), or $R^1$ is 3-pyridinyl (which may bear a methyl, fluoro or chloro substituent at the 6-position), or $R^1$ is phenyl (which may bear one, two or three substituents at the 3-, 4- or 5-position(s) independently selected from halo, cyano, carbamoyl, methyl, methoxy., difluoromethoxy, hydroxymethyl, formyl, vinyl, amino, hydroxy and 3, 4-methylenedioxy; and in addition the phenyl may bear a 2-chloro or 2-fluoro substituent), or $R^1$ is 6-indolyl (which may bear a chloro or methyl substituent at the 3-position), or $R^1$ is 6-indazolyl (which may bear a methyl substituent at the 3-position);

$A^3, A^4, A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$;

wherein $R^3$ is hydrogen, fluoro, chloro, methyl, methoxy, hydroxy or carboxy;

one of $R^4$ and $R^5$ is hydrogen, (1–4C)alkyl, halo, trifluoromethyl, trifluoromethoxy, cyano, hydroxymethyl, (1–3C)acyl, $R^fO$—, $R^fO_2C$—, $R^fO_2C$—$CH_2$—, $R^fO_2C$—$CH_2$—O—, methylthio or $R^gNH$—;

the other of $R^4$ and $R^5$ is hydrogen, halo or methyl; and $R^6$ is hydrogen, fluoro, chloro, methyl or methoxy;

in which $R^f$ is hydrogen, (1–4C)alkyl or benzyl; $R^g$ is hydrogen, (1–3C)acyl, trifluoroacetyl, methoxyacetyl, or $R^hSO_h$— (wherein h is 1 or 2); and $R^h$ is (1–4C)alkyl, trifluoromethyl, phenyl, amino, methylamino or dimethylamino; or $A^3, A^4, A^5$ and $A^6$, together with the two carbons to which they are attached, complete a substituted heteroaromatic ring in which (a) one of $A^3, A^4, A^5$ and $A^6$ is N, and each of the others is $CR^3, CR^4, CR^5$ or $CR^6$, respectively; wherein each of $R^3, R^4, R^5$ and $R^6$ is independently hydrogen or methyl, or one of $R^3, R^4, R^5$ and $R^6$ attached to a carbon which is not bonded to an N-atom is chloro and the others are hydrogen; or (b) two adjacent residues of $A^3, A^4, A^5$ and $A^6$ together form S, and each of the others is $CR^3, CR^4, CR^5$ or $CR^6$, respectively; wherein each of $R^3, R^4, R^5$ and $R^6$ is hydrogen, or one or two of $R^3, R^4, R^5$ and $R^6$ is independently chloro, bromo or methyl and the others are hydrogen; or (c) $A^3$ and $A^4$ together form a fused benz ring, and $A^5$ and $A^6$ together form —NH—;

L is carbonyl or methylene; M is N and Q (showing L and M at the points of attachment) is a residue of formula $Q^A$,

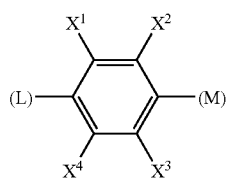

in which each of $X^1$, $X^2$, $X^3$ and $X^4$ is hydrogen; or $X^1$ is $OR^Q$ and each of $X^2$, $X^3$ and $X^4$ is hydrogen in which $R^Q$ is hydrogen, (1–3C)alkyl, (3–6C)cycloalkyl, 2-hydroxyethyl, 2-methoxyethyl or 2-methylthioethyl; or one of $X^1$ and $X^2$ is trifluoromethyl; and each of the others of $X^1$, $X^2$, $X^3$ and $X^4$ is hydrogen; or one or two of $X^2$ and $X^3$ is fluoro; and each of the others of $X^1$, $X^2$, $X^3$ and $X^4$ is hydrogen; or L is carbonyl or methylene; M is N; and Q is cyclohexan-1,4-diyl; or L is carbonyl or methylene; M is CH and Q is piperidin-1,4-diyl which is bonded to L at the 4-position and is bonded to M at the 1-position; or L is carbonyl; M is N and Q is piperidin-1,4-diyl which is bonded to L at the 1-position and is bonded to M at the 4-position; and R is hydrogen, (1–3C)alkyl, (3–5C)cycloalkyl, (1–3C) acyl, acetyloxyacetyl, aminoacetyl, hydroxyacetyl, {(1–4C) alkoxy}carbonyl, {(1–4C) alkoxy}carbonylmethyl, $R^aR^bN$—CO— or $R^jSO_j$—, wherein each of $R^a$ and $R^b$ is independently hydrogen or (1–3C)alkyl, or $R^aR^bN$— is 1-azetidinyl, 1-pyrrolidinyl, 1-piperidinyl, 4-morpholinyl, or 4-thiomorpholinyl; j is 1 or 2; and $R^j$ is (1–4C)alkyl, trifluoromethyl, amino, methylamino or dimethylamino.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values are listed below for radicals, substituents, and ranges, for illustration only, and they do not exclude other defined values or other values within defined ranges for the radicals and substituents. Thus, a particular value for halo is fluoro, chloro or bromo; for (1–3C)alkyl is methyl, ethyl, propyl or isopropyl; for (1–4C)alkyl is methyl, ethyl, propyl, isopropyl, butyl, isobutyl or t-butyl; for (3–5C)cycloalkyl is cyclopropyl, cyclobutyl or cyclopentyl; for (3–6C)cycloalkyl is cyclopropyl, cyclopentyl or cyclohexyl; for (1–4C)alkoxy is methoxy, ethoxy, propoxy, isopropoxy, butoxy, isobutoxy or t-butoxy; and for (1–3C) acyl is formyl, acetyl or propionyl.

A particular compound of formula I is one wherein:

$R^1$ is 2-pyridinyl (which may bear a methyl, methoxy, methylthio, fluoro or chloro substituent at the 5-position), or $R^1$ is 3-pyridinyl (which may bear a methyl, fluoro or chloro substituent at the 6-position), or $R^1$ is phenyl (which may bear a substituent at the 3- or 4-position(s) independently selected from halo, cyano, carbamoyl, methyl, methoxy, difluoromethoxy, hydroxymethyl, formyl, vinyl, amino, hydroxy and 3,4-methylenedioxy), or $R^1$ is 6-indolyl (which may bear a chloro or methyl substituent at the. 3-position);

$A^3$ is $CR^3$, $A^4$ is $CR^4$, $A^5$ is $CR^5$, and $A^6$ is $CR^6$; wherein $R^3$ is hydrogen;

one of $R^4$ and $R^5$ is hydrogen, (1–4C)alkyl, halo, trifluoromethyl, trifluoromethoxy, cyano, hydroxymethyl, (1–3C) acyl, $R^fO$—, $R^fO_2C$—, $R^fO_2C$—$CH_2$—, $R^fO_2C$—$CH_2$—O—, methylthio or $R^gNH$— in which $R^g$ is hydrogen, (1–3C)acyl, or $R^hSO_2$—; and $R^h$ is (1–4C)alkyl, trifluoromethyl, amino, methylamino or dimethylamino;

the other of $R^4$ and $R^5$ is hydrogen, halo or methyl; and $R^6$ is hydrogen; or $A^3$ is N, and each of $A^4$, $A^5$ and $A^6$ is $CR^4$, $CR^5$ and $CR^6$, respectively, in which each of $R^4$ and $R^6$ is hydrogen and $R^5$ is hydrogen, chloro or methyl; or $A^6$ is N, and each of $A^3$, $A^4$ and $A^5$ is $CR^3$, $CR^4$ and $CR^5$, respectively, in which each of $R^3$ and $R^4$ is hydrogen and $R^5$ is hydrogen or methyl; and R is hydrogen, methyl, ethyl, acetyl, acetoxyacetyl, hydroxyacetyl, methylsulfonyl or dimethylaminosulfonyl.

A more particular compound, or salt thereof, as described above in one wherein:

$R^1$ is 2-pyridinyl which bears a methyl or chloro substituent at the 5-position, $A^3$ is $CR^3$, $A^4$ is $CR^4$, $A^5$ is $CR^5$, and $A^6$ is $CR^6$ wherein each of $R^3$, $R^4$ and $R^6$ is hydrogen and $R^5$ is fluoro, chloro or methyl; or $A^3$ is N, and each of $A^4$, $A^5$ and $A^6$ is CH; or $A^6$ is N, and each of $A^3$, $A^4$ and $A^5$ is CH; and R is hydrogen or methyl.

One particular compound, or salt thereof, according to any of the above descriptions is one wherein Q is $Q^4$; and more particularly wherein Q is $Q^4$ in which:

each of $X^1$, $X^2$, $X^3$ and $X^4$ is hydrogen; or $X^1$ is $OR^Q$ and each of $X^2$, $X^3$ and $X^4$ is hydrogen in which $R^Q$ is hydrogen, (1–3C)alkyl, (3–6C)cycloalkyl, 2-methoxyethyl or 2-methylthioethyl; or $X^1$ is trifluoromethyl and each of $X^2$, $X^3$ and $X^4$ is hydrogen; or $X^2$ is trifluoromethyl and each of $X^1$, $X^3$ and $X^4$ is hydrogen; or $X^2$ is fluoro and each of $X^1$, $X^3$ and $X^4$ is hydrogen; or each of $X^2$ and $X^3$ is fluoro and each of $X^1$ and $X^4$ is hydrogen.

One such compound of formula I is one wherein each of $X^1$, $X^2$, $X^3$ and $X^4$ is hydrogen.

Another such compound of formula I is one wherein $X^1$ is $OR^Q$ and each of $X^2$, $X^3$ and $X^4$ is hydrogen in which $R^Q$ is hydrogen, ethyl, isopropyl, 2-hydroxyethyl, 2-methoxyethyl or 2-methylthioethyl.

Another such compound of formula I is one wherein $X^1$ is trifluoromethyl and each of $X^2$, $X^3$ and $X^4$ is hydrogen.

Another such compound of formula I is one wherein $X^2$ is trifluoromethyl and each of $X^1$, $X^3$ and $X^4$ is hydrogen.

Another such compound of formula I is one wherein each of $X^2$ and $X^3$ is fluoro and each of $X^1$ and $X^4$ is hydrogen.

Another particular compound, or salt thereof, according to any of the above descriptions is one wherein Q is cyclohexan-1,4-diyl.

A further particular compound, or salt thereof, according to any of the above descriptions is one wherein Q is piperidin-1,4-diyl which is bonded to L at the 4-position and is bonded to M at the 1-position.

For any of the above descriptions a more particular compound or salt thereof of formula I is one where L is carbonyl.

Another more particular compound, or salt thereof, for any of the above descriptions is one wherein L is methylene.

An additional particular compound, or salt thereof, according to any of the above descriptions is one wherein Q is piperidin-1,4-diyl which is bonded to L at the 1-position and is bonded to M at the 4-position.

A specific compound, or salt thereof, wherein Q is $Q^A$ is any one of those provided in the Examples, especially that of Example 4, 8, 9, 10, 18, 19 or 21.

A pharmaceutically acceptable salt of a compound of the instant invention is one which is the acid addition salt of a basic compound of formula I with an inorganic or organic acid which affords a physiologically acceptable anion or which is the salt formed by an acidic compound of formula I with a base which affords a physiologically acceptable cation and provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a compound of formula I (or a pharmaceutically acceptable salt thereof) as provided in any of the descriptions herein.

In addition, there is provided the use of a compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a compound of formula I having any of the definitions herein.

The present invention further provides a method of inhibiting factor Xa comprising administering to a mammal in need of treatment, a factor Xa inhibiting dose of compound of formula I having any of the definitions herein.

Further, the present invention provides a method of treating a thromboembolic disorder comprising administering to a mammal in need of treatment, an effective dose of a compound of formula I having any of the definitions herein.

Also, there is provided a compound of formula I (or prodrug or salt) having any of the definitions herein for use as an antithrombotic agent.

In addition, there is provided the use of a compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a compound of formula I (or of a pharmaceutically acceptable salt thereof) as provided in any of the descriptions herein.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, which comprises:

(A) for a compound of formula I in which Q is $Q^A$, substituting the group $Y^a$ of a compound of formula II,

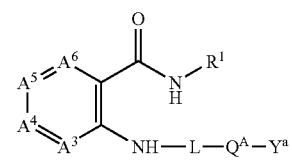

II in which $Y^a$ is a leaving group for nucleophilic aromatic substitution, using an amine of formula III,

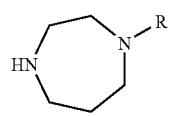

III (B) for a compound of formula I in which L is carbonyl, acylating an amine of formula IV

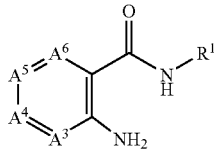

using a corresponding acid of formula V,

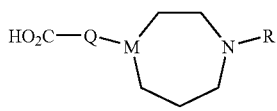

or an activated derivative thereof;

(C) for a compound of formula I in which R is not hydrogen, substituting the nitrogen of a corresponding compound in which R is hydrogen using a conventional procedure;

(D) for a compound of formula I in which L is methylene, substituting the group $Y^a$ of a compound of formula VI

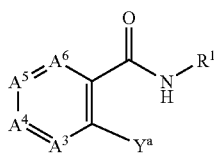

in which $Y^a$ is a leaving group for nucleophilic aromatic substitution with an amine of formula VII; or

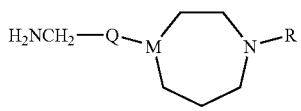

alkylating an amine of formula IV directly, using a compound of formula VIII,

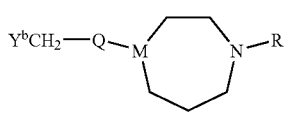

in which $Y^b$ is a leaving group for nucleophilic substitution, or indirectly by reductive alkylation using an aldehyde of formula IX;

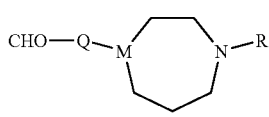

(E) acylating an amine of formula $H_2N-R^1$, or a deprotonated derivative thereof, using an acid of formula X,

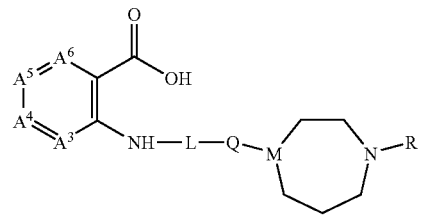

or an activated derivative thereof; or (F) for a compound of formula I in which Q is cyclohexan-1,4-diyl or Q is piperidin-1,4-diyl which is bonded to L at the 1-position, reductively alkylating an amine of formula III using a compound of formula XIa or XIb, respectively;

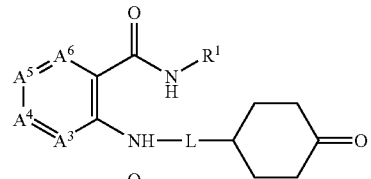

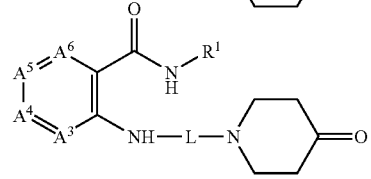

(G) for a compound of formula I in which Q is piperidin-1,4-diyl which is bonded to L at the 4-position, reductively alkylating an amine of formula XII

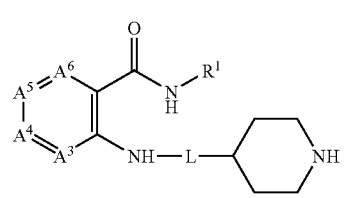

using a compound of formula XIII;

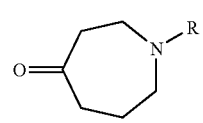

whereafter, for any of the above procedures, when a functional group of a starting material is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $R^1$, $A^3$–$A^6$, L, M, Q, and R have any of the values defined in any of-the above definitions.

As used herein, a leaving group "$Y^a$" is a moiety which is displaced in an aromatic (or heteroaromatic) nucleophilic substitution reaction, for example a halo group (such as fluoro or chloro), an alkoxy group (such as methoxy), a sulfonate ester group (such as methylsulfonyloxy, p-toluylsulfonyloxy or trifluoromethylsulfonyloxy), or the reactive species derived from treating an alcohol with triphenylphosphine, diethyl azodicarboxylate and triethyl amine (in a Mitsunobu reaction). The substitution may be carried out by heating a mixture of the reagents in a polar solvent, for example in dimethyl sulfoxide in a sealed tube or vial as described at Example 5, Example 18a, and Example 22.

For a carboxylic acid, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or anhydride derived from a coupling reagent), as well as (when the product is a urea) the isocyanate. Typical procedures include those described for preparation of intermediate compounds at Intermediate A-2 and Example 23-A, as well as the O-protected product of Example 17.

For a compound of formula I in which R is (1-C)alkyl or {(1–4C)alkoxy}carbonylmethyl, a conventional procedure for substituting the nitrogen of a compound in which R is hydrogen comprises alkylating the nitrogen, for example by reductively alkylating the nitrogen with the requisite aldehyde or ketone or by alkylating the nitrogen with a reagent of formula R-$Y^b$, in which $Y^b$ is a leaving group for nucleophilic substitution.

For a compound of formula I in which R is (1–3C)acyl, acetyloxyacetyl, aminoacetyl, hydroxyacetyl, {(1–4C)alkoxy}-carbonyl or $R^aR^bN$—CO—, a conventional procedure for substituting the nitrogen of a compound in which R is hydrogen comprises acylating the nitrogen using the requisite carboxylic acid or activated derivative thereof (in which a functional group may be protected, followed by removal of the protecting group).

For a compound of formula I in which R is $R^jSO_j$—, a conventional procedure for substituting the nitrogen of a compound in which R is hydrogen comprises treating the amine with the requisite sulfinyl or sulfonyl halide, for example using the chloride of formula $R^jSO_j$—Cl.

As used herein, a leaving group "$Y^b$" is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphosphine, diethyl azodicarboxylate and triethyl amine (in a Mitsunobu reaction).

A novel intermediate or starting material compound provides a further aspect of the invention. The various starting materials may be made by processes which include processes known in the chemical art for the production of structurally analogous compounds or by a novel process described herein or one analogous thereto.

Thus, one particular intermediate is a compound of formula II,

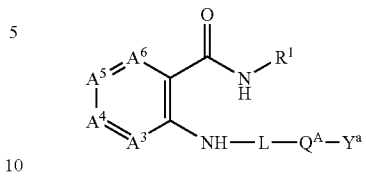

II in which $Y^a$ is a leaving group for nucleophilic aromatic substitution and $R^1$, $A^3$–$A^6$, L and $Q^A$ have any of the values defined in any of the above definitions, or a derivative thereof in which a functional group other than $Y^a$ is protected using a protecting group. It is preferred that the intermediate of formula II be one in which L is carbonyl.

Another intermediate is an acid of formula V,

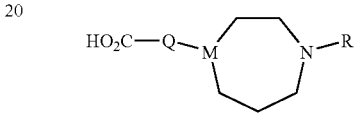

V or an activated derivative thereof, or a salt of the acid or activated derivative, in which Q and R have any of the values defined in any of the above definitions, or a derivative thereof in which a functional group other than the carboxy group, or activated derivative thereof, is protected using a protecting group.

A further intermediate is an amine of formula VII, or a salt thereof; or

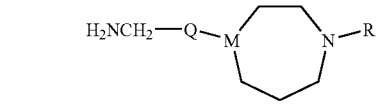

VII a compound of formula VIII, or a salt thereof,

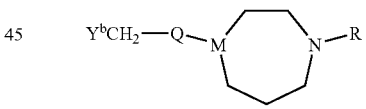

VIII in which $Y^b$ is a leaving group for nucleophilic substitution, or an aldehyde of formula IX, or a salt thereof;

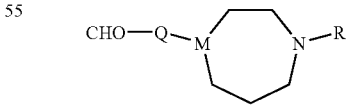

IX in which M, Q and R have any of the values defined in any the above definitions, or a derivative thereof in which a functional group other than the primary amino group of the compound of formula VII, the leaving group of the compound of formula VIII, or the aldehyde group of the compound of formula IX, respectively, is protected using a protecting group.

Another intermediate is an acid of formula X,

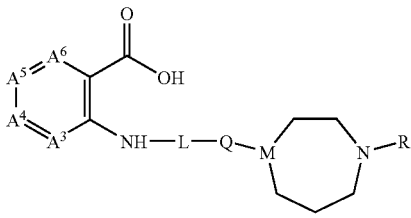

or an activated derivative thereof, or a salt of the acid or activated derivative, in which $A^3$–$A^6$, L, M, Q and R have any of the values defined in any of the above definitions, or a derivative thereof in which a functional group other than the carboxy group, or activated derivative thereof, is protected using a protecting group; and more particularly the acid of formula X in which L is carbonyl.

For an acid of formula X in which L is carbonyl, a particular activated derivative is a compound of formula Xa

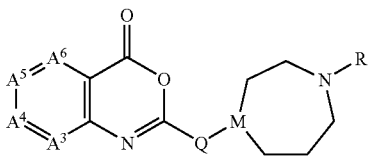

and for an acid of formula X in which L is methylene, a particular activated derivative is a compound of formula Xb

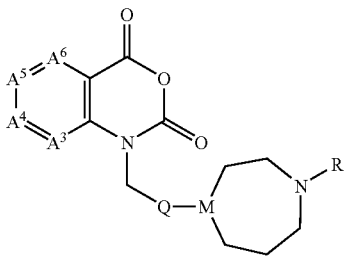

or a salt of the activated derivative, in which $A^3$–$A^6$, M, Q and R have any of the values defined in any of the above descriptions, or a derivative thereof in which a functional group other than the activated derivative of the carboxy group is protected using a protecting group.

A further particular intermediate is a compound of formula XIa,

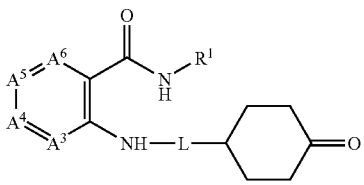

or a salt thereof, wherein $R^1$, $A^3$–$A^6$ and L have any of the values defined in any of the above descriptions; and, more particularly, the compound, or salt thereof, in which L is carbonyl.

As a further aspect of the invention, there is provided the use of a compound (or activated and/or protected derivative thereof or salt of the compound or derivative) of formula II, V, VII, VIII, IX, X or XIa as a starting material in the preparation of an inhibitor of factor Xa.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which there is a hydroxy, but in which the corresponding substituent is —$OP^p$ in place of hydroxy, wherein $P^p$ is a phenol protecting group other than methyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in a mammal comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., *Lung*, (1999), 177(4), 253–262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation. The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably, the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |

-continued

| | |
|---|---|
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

The ability of a compound of the present invention to be an effective and orally active factor Xa inhibitor may be evaluated-in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

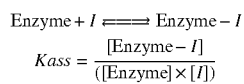

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: In each well is placed 50 μL buffer (0.06 M Tris, 0.3 M NaCl, pH 7.4), followed by 25 μL of inhibitor solution (in 100% methanol) and 25 μL enzyme solution (e.g., human factor Xa, 32 nM in 0.03 M Tris, 0.15 M NaCl, 1 mg/mL HAS); finally, within two minutes, 150 μL aqueous solution of chromogenic substrate (e.g., 0.3 mM BzIle-Glu-Gly-Arg-pNA) is added to start the enzymatic reaction. Final factor Xa concentration is 3.2 nM. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, human factor Xa is used to hydrolyze BzIle-Glu-Gly-Arg-pNA; 5.9 nM human thrombin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a factor Xa inhibiting compound of formula I of the instant invention, as exemplified herein, exhibits a Kass of greater than $10^6$ L/mole and a compound of formula I in which Q is $Q^4$ exhibits a Kass of $10 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention potently extended the prolongation times in the APTT and PT assays, for example in some cases, with assay concentrations necessary to double the APPT or PT of less than 1 μM.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2–3%, conveniently 2.5%, for surgery; 1.5–2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Ex Vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, Organon Teknika) are incubated for 5 minutes (37° C.); and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acaia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes befoe the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthesized rabbit, for example an infusion rate of 6.8 mL/h was used for one compound infused in 5% PEG200 in water.

Statistics

Results are expressed as means+/– SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months-2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model.

Test compound is formulated immediately prior to dosing by making a suspension in a "wet granulaion" (povidone, 0.85 mg/mL; lactose, 15.0 mg/mL; and polysorbate 80, 65 μL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, VD; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is fomulated immediately prior to dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate: 9 parts blood) is drawn before drug administration, at 60 min after administration, at 60 min after initiation of vessel injury and just prior to the end of the experiment. Whole blood cell counts, hemoglobin, and hematocrit values are determined on a 40-μL sample of the citrated whole blood with a hematology analyzer (Cell-Dyn 900, Sequoia-Turner, Mount View, Calif., U.S.A.). The remaining blood was cetrifuged at 3,000 g for 5 min to prepare cell-free plasma. Plasma clotting times, prothrombin time (PT) and activated partial thromoplastin times (APTT) were performed using standard Dade reagents and the Coa-Screener coagulation device (American Labor, Largo, Fla.). Gingival template bleeding times are determined with a Simplate II bleeding time device (organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

Compounds of the instant invention are potent anticoagulant and antithrombotic agents which exhibit particularly good plasma exposure following oral administration, as well as desirable volume of distribution and tissue selectivity properties, as evidenced by standard pharmacokinetic/pharmcodynamic and brain flux assays.

The following Examples are provided to further describe the invention and are not to be construed as limitations thereof.

The abbreviations, symbols and terms used in the examples have the following meanings.

Ac=acetyl
Analysis=elemental analysis
aq=aqueous
Boc=t-butyloxycarbonyl
Calcd=calculated
conc=concentrated
DMF=dimethylformamide
DMSO=dimethylsulfoxide
EtOAc=ethyl acetate
EtOH=ethanol
MeOH=methanol
HPLC=High Performance Liquid Chromatography
IR=Infrared Spectrum
APCI-MS=atmospheric pressure chemical ionization mass spectrum
ESI-MS (or ES-MS)=electrospray ionization mass spectrum
FD-MS=field desorption mass spectrum
IS-MS=ion spray mass spectrum
NMR=Nuclear Magnetic Resonance
RPHPLC=Reversed Phase High Performance Liquid Chromatography
RT (or Rt)=retention time
satd=saturated
SCX=strong cation exchange (resin)
TFA=trifluoroacetic acid
THF=tetrahydrofuran Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

Analytical HPLC method was a linear gradient of 90/10 to 50/50 (0.1% TFA in water/0.1% TFA in acetonitrile) over 40 minutes with a flow rate of 1 mL/min.

PREPARATION OF NITRO-AMIDE (NA) INTERMEDIATES

General Procedure NA-A:

2-Nitro-N-(5-methylpyridin-2-yl)benzamide.

To a stirring solution of 2-amino-5-methylpyridine (3.1 g, 29 mmol) in dichloromethane (200 mL) was added pyridine (7.3 mL, 90 mmol) followed by 2-nitrobenzoyl chloride (5.7 g, 30 mmol). After 4 h, the solvent was removed in vacuo and the residue was partitioned between ethyl acetate (500 mL) and water (250 mL). The organic phase was separated and washed with water, brine, dried (MgSO$_4$) and filtered, and then concentrated in vacuo to a volume of about 100 mL (precipitate observed). The mixture was then sonicated and allowed to stand overnight then filtered. The collected solid was then washed with diethyl ether, filtered and dried under vacuum to give 3.9 g (52%) of the title compound.

$^1$H-NMR
FD-MS, m/e 256.9 (M+).
Analysis for C$_{13}$H$_{11}$N$_3$O$_3$: Calc: C, 60.70; H, 4.31; N, 16.33; Found: C, 61.21; H, 4.32; N, 16.63.

General Procedure NA-B:

4-Chloro-N-(5-chloropyridin-2-yl)-2-nitrobenzamide.

To a stirring suspension of 4-chloro-2-nitrobenzoic acid (20 g, 99 mmol) in dichloromethane (500 mL) was added a few drops of DMF, followed by oxalyl chloride (15.1 g, 119 mmol). After 1.h, the solvent was removed in vacuo and the residue was dissolved in dichloromethane (500 mL). To this stirring solution was added pyridine (24 mL, 297 mmol) followed by 2-amino-5-chloropyridine (12.7 g, 99 mmol). After stirring overnight, the solvents were removed in vacuo and the residue was stirred vigorously with ethyl acetate and water for several hours. The mixture was filtered to give a white solid, which was washed with ethyl acetate and dried in vacuo to give 23 g (74%) of the title compound. The combined ethyl acetate washings and extract were then washed twice with 1 M citric acid, once with brine, twice with saturated aq sodium bicarbonate, and again with brine. The organic phase was then dried with MgSO$_4$, filtered and concentrated in vacuo. The solid was then suspended in diethyl ether, sonicated and filtered to give a second crop of the title compound as a white solid (5.79 g, 19%).

$^1$H-NMR
IS-MS, m/e 312.0 (M+1)
Analysis for C$_{12}$H$_7$N$_3$O$_3$Cl$_2$: Calcd: C, 46.18;.H, 2.26; N, 13.46; Found: C, 46.24; H, 2.37; N, 13.43.

Preparation of Intermediates NA-1-NA-12

The following exemplary nitro-amide intermediates were prepared using a conventional procedure such as that of General Procedure NA-A or General Procedure NA-B, or as otherwise described.

Intermediate NA-1

5-Fluoro-2-nitro-N-(5-fluoropyridin-2-yl)benzamide.

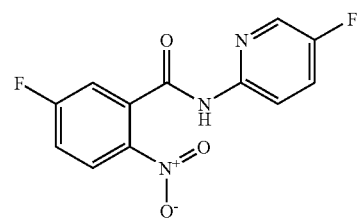

$^1$H-NMR
ESI-MS, m/e 278.09 (M−1).
The starting 4-fluoro-2-nitrobenzoic acid was prepared as follows:

To a stirring solution of KMnO$_4$ (76 g, 483 mmol) in water (1 L) was added 4-fluoro-2-nitrotoluene and the solution was heated to reflux. After 4 h, the hot mixture was filtered and the filtrate was cooled with ice, washed with diethyl ether, acidified with conc HCl, and then extracted twice with diethyl ether. The combined ether extracts were washed with brine, dried with MgSO$_4$, filtered and concentrated in vacuo to give 12.07 g (34%) of a white solid.

$^1$H-NMR

IS-MS, m/e 184.0 (M−1).

Analysis for C$_7$H$_4$NO$_4$F: Calcd: C, 45.42; H, 2.18; N, 7.57; Found: C, 45.63; H, 2.30; N, 7.61.

Intermediate NA-2

5-Fluoro-2-nitro-N-(5-chloropyridin-2-yl)benzamide.

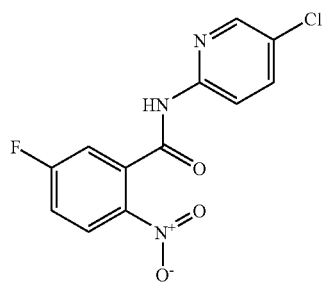

$^1$H-NMR

ESI-MS, m/e 296.22 (M+1).

Analysis for C$_{12}$H$_7$ClFN$_3$O$_3$: Calcd: C,48.75; H,2.39; N,14.21; Found: C,48.57; H,2.37; N,14.19.

Intermediate NA-3

5-Chloro-2-nitro-N-(5-fluoropyridin-2-yl)benzamid.

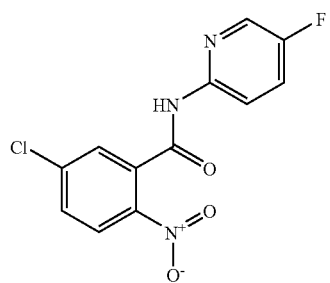

$^1$H-NMR

ESI-MS, m/e 296.24 (M+1).

Analysis for C$_{12}$H$_7$ClFN$_3$O$_3$: Calcd: C, 48.75; H, 2.39; N, 14.21; Found: C, 48.97; H, 2.61; N, 14.13.

Intermediate NA-4

5-Chloro-2-nitro-N-(5-chloropyridin-2-yl)benzamide.

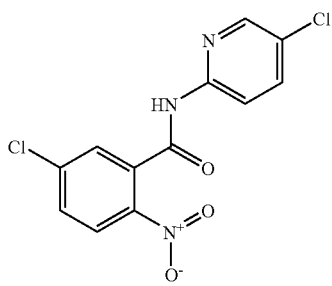

$^1$H-NMR

ESI-MS, m/e 311.96 (M+1).

Analysis for C$_{12}$H$_7$Cl$_2$N$_3$O$_3$: Calcd: C, 46.18; H, 2.26; N, 13.46; Found: C, 46.24; H, 2.22; N, 13.29.

Intermediate NA-5

5-Chloro-2-nitro-N-(5-methylpyridin-2-yl)benzamide.

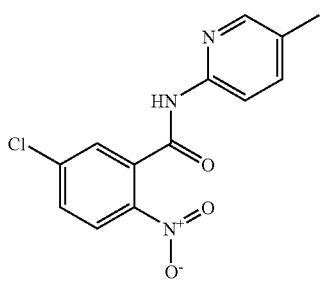

$^1$H-NMR

ESI-MS, m/e 291.97 (M+1).

Analysis for C$_{13}$H$_{10}$ClN$_3$O$_3$: Calcd: C, 53.53; H, 3.46; N, 14.41; Found: C, 53.76; H, 3.41; N, 14.35.

Intermediate NA-6

5-Methyl-2-nitro-N-(5-fluoropyridin-2-yl)benzamide.

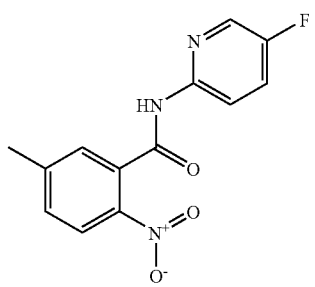

$^1$H-NMR

APCI-MS, m/e 276 (M+1).

Intermediate NA-7

5-Methyl-2-nitro-N-(5-chloropyridin-2-yl)benzamide.

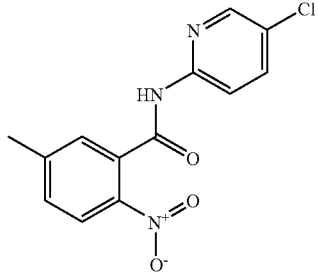

¹H-NMR
ESI-MS, m/e 292 (M+1).
Analysis for $C_{13}H_{10}ClN_3O_3$: Calcd: C, 53.53; H, 3.46; N, 14.41; Found: C, 53.52; H, 3.56; N, 14.49.

Intermediate NA-8

5-Methyl-2-nitro-N-(5-methylpyridin-2-yl)benzamide.

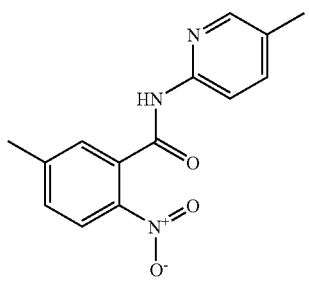

¹H-NMR
ESI-MS, m/e 272.37 (M+1).

Intermediate NA-9

4,5-Difluoro-2-nitro-N-(5-chloropyridin-2-yl)benzamide.

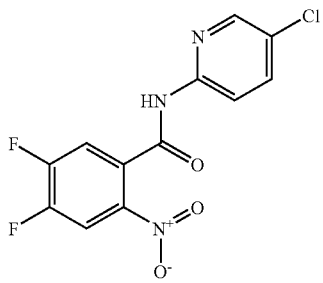

¹H-NMR
ESI-MS, m/e 313.95 (M+1).
Analysis for $C_{12}H_6ClF_2N_3O_3$: Calcd: C, 45.95; H, 1.93; N, 13.40; Found: C, 45.77; H, 2.00; N, 13.43.

Intermediate NA-10

Compound AA-10 prepared via 4-amino-3-iodoacetophenone

Intermediate NA-11

4-Methoxycarbonyl-2-nitro-N-(5-chloropyridin-2-yl)benzamide.

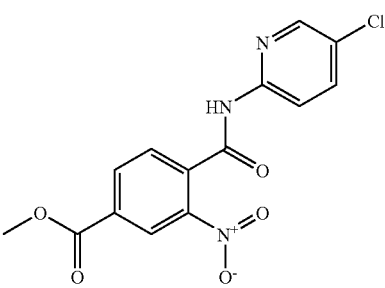

¹H-NMR
ESI-MS, m/e 336.09 (M+1).
Analysis for $C_{14}H_{10}ClN_3O_5$: Calcd: C, 50.09; H, 3.00; N, 12.52; Found: C, 49.83; H, 3.08; N, 12.25.

Intermediate NA-12

5-Methoxycarbonyl-2-nitro-N-(5-chloropyridin-2-yl)benzamide.

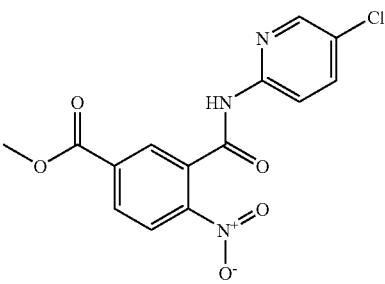

¹H-NMR
ESI-MS, m/e 336.07 (M+1).
Analysis for $C_{14}H_{10}ClN_3O_5$: Calcd: C, 50.09; H, 3.00; N, 12.52; Found: C, 50.37; H, 3.08; N, 12.52.

Preparation of Amino-Amide (AA) Intermediates

General Procedure AA-A:

N-(5-Methylpyridin-2-yl)-2-aminobenzamide.

To a stirring solution of N-(5-methylpyridin-2-yl)-2-nitrobenzamide (1.5 g, 5.8 mmol) and Ni(OAc)$_2$·4H$_2$O (2.9 g, 11.7 mmol) in THF (20 mL) and methanol (40 mL) at 0° C. was added, in small portions, sodium borohydride (0.88 g, 23.2 mmol). After complete addition and an additional 5 min, the solvent was evaporated in vacuo and the residue was partitioned between ethyl acetate (200 mL) and 50% conc NH$_4$OH (206 mL). The organic phase was separated and washed again with 50% conc NH$_4$OH, followed by brine, then dried with MgSO$_4$, filtered and concentrated in vacuo to give 1.25 g (95%) of a light yellow solid.

$^1$H-NMR

FD-MS, m/e 227.1 (M+).

General Procedure AA-B:

N-(5-Chloropyridin-2-yl)-2-aminobenzamide.

To a solution of N-(5-chloropyridin-2-yl)-2-nitrobenzamide (2 g, 7.2 mmol) in THF (50 mL) and ethyl acetate (50 mL) was added Raney Ni (0.2 g) and the mixture was placed under hydrogen (4.1 bar) in a high pressure apparatus. After shaking overnight, the mixture was filtered and concentrated in vacuo and purified by flash chromatography to give 1.5 g (83%) of an off-white solid.

$^1$H-NMR

Preparation of Intermediates AA-1-AA-14

The following exemplary amino-amide intermediates were prepared using a conventional procedure such as that of General Procedure AA-A or General Procedure AA-B, or as otherwise described.

Intermediate AA-1

2-Amino-5-fluoro-N-(5-fluoropyridin-2-yl)benzamide.

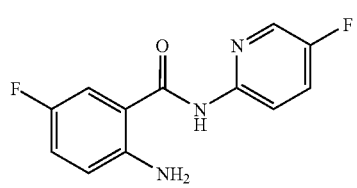

$^1$H-NMR

ESI-MS, m/e 248 (M−1)

Intermediate AA-2

2-Amino-5-fluoro-N-(5-chloropyridin-2-yl)benzamide.

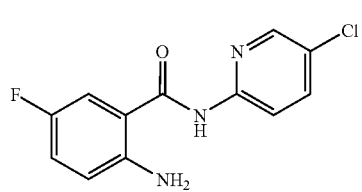

$^1$H-NMR

ESI-MS, m/e 264.17 (M−1).

Analysis for C$_{12}$H$_9$ClFN$_3$O: Calcd: C, 54.25; H, 3.41; N, 15.82; Found: C, 53.96; H, 3.43; N, 15.54.

Intermediate AA-3

2-Amino-5-chloro-N-(5-fluoropyridin-2-yl)benzamide.

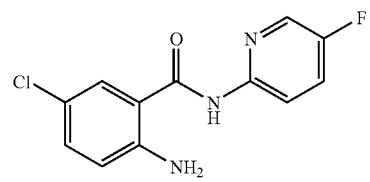

$^1$H-NMR

ESI-MS, m/e 264.13 (M−1).

Intermediate AA-4

2-Amino-5-chloro-N-(5-chloropyridin-2-yl)benzamide.

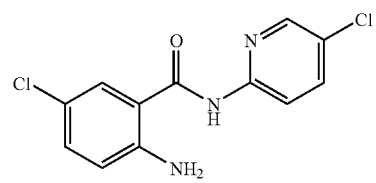

$^1$H-NMR

ESI-MS, m/e 281.12 (M−1).

Analysis for C$_{12}$H$_9$Cl$_2$N$_3$O: Calcd: C, 51.09; H, 3.22; N, 14.89; Found: C, 51.19; H, 3.33; N, 14.61.

Intermediate AA-5

2-Amino-5-chloro-N-(5-methylpyridin-2-yl)benzamide.

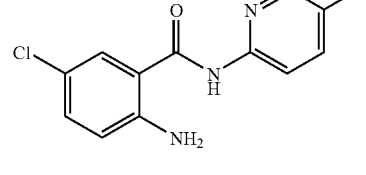

$^1$H-NMR

ESI-MS, m/e 260.02 (M−1).

Analysis for C$_{13}$H$_{12}$ClN$_3$O: Calcd: C, 59.66; H, 4.62; N, 16.06; Found: C, 59.89; H, 4.57; N, 15.99.

Intermediate AA-6

2-Amino-5-methyl-N-(5-fluoropyridin-2-yl)benzamide.

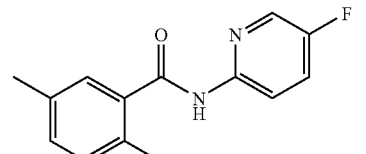

$^1$H-NMR

ESI-MS, m/e 244.41 (M−1).

Intermediate AA-7

2-Amino-5-methyl-N-(5-chloropyridin-2-yl)benzamide.

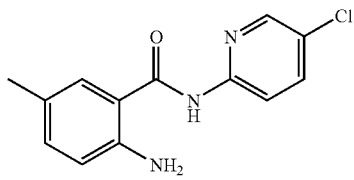

¹H-NMR
ESI-MS, m/e 260.01 (M−1).

Intermediate AA-8

2-Amino-5-methyl-N-(5-methylpyridin-2-yl)benzamide.

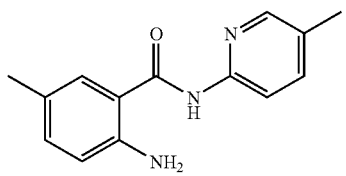

¹H-NMR
ESI-MS, m/e 240.15 (M−1).

Intermediate AA-9

2-Amino-4,5-difluoro-N-(5-chloropyridin-2-yl)benzamide.

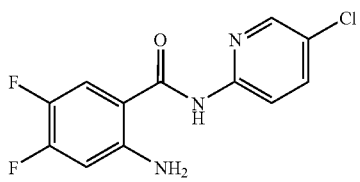

¹H-NMR
ESI-MS, m/e 282.12 (M−1).

Intermediate AA-10

5-Acetyl-2-amino-N-(5-chloropyridin-2-yl)benzamide.

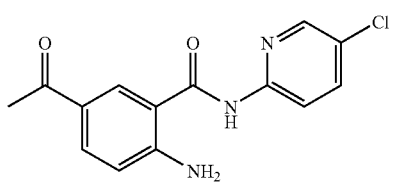

To a stirred solution of 4-aminoacetophenone (50 g, 370 mmol) in ethanol (1 L) and dichloromethane (750 mL) at 0° C. was added iodine (94 g, 370 mmol) and silver sulfate (116 g, 370 mmol). The reaction mixture was stirred at 0° C. for 10 min and then at room temperature for 4 h, filtered and concentrated. The resulting residue was partitioned between dichloromethane and 5 N sodium hydroxide. The organic phase was dried (magnesium sulfate), filtered, and concentrated in vacuo. The crude product was chromatographed over silica gel, eluting with a stepwise gradient from dichloromethane to 10% ethyl acetate in dichloromethane, to give 38.2 g (40%) of 4-amino-3-iodoacetophenone as a yellow oil.

A mixture of 4-amino-3-iodoacetophenone (5.0 g, 19.2 mmol), 2-amino-5-chloropyridine (7.4 g, 54.5 mmol), palladium acetate (431 mg, 1.92 mmol), 1,3-bis(diphenylphosphino)propane (2.37 g, 5.75 mmol), triethylamine (5.4 mL, 38.3 mmol) in acetonitrile (100 mL) was shaken under a carbon monoxide atmosphere (54.4 bar) for 16 h. The crude mixture was filtered through diatomaceous earth, and the filtrate was stripped to near dryness and titurated with ethyl ether to remove the excess 2-amino-5-chloropyridine. The product was isolated by SCX column, then flash chromatography using 10% acetonitrile in chloroform. This afforded 1.17 g (21%) of the title product.

¹H-NMR
ESI-MS, m/e 288.1 (M−1).

Intermediate AA-11

2-Amino-4-methoxycarbonyl-N-(5-chloropyridin-2-yl)benzamide.

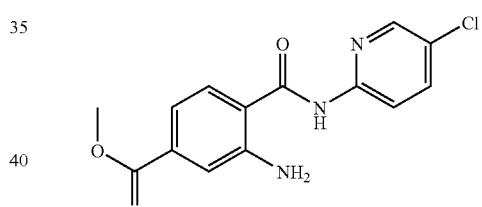

¹H-NMR
ESI-MS, m/e 304.09 (M−1).

Intermediate AA-12

2-Amino-5-methoxycarbonyl-N-(5-chloropyridin-2-yl)benzamide.

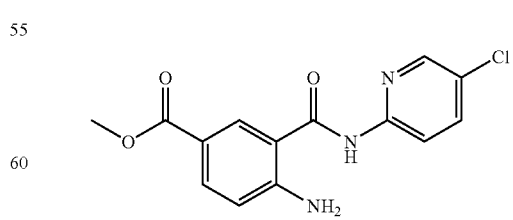

¹H-NMR
ESI-MS, m/e 304 (M−1).

Intermediate AA-13

3-Amino-N-(5-chloropyridin-2-yl)pyridine-2-carboxamide.

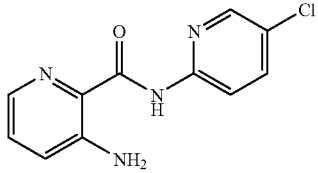

$^1$H-NMR

ESI-MS, m/e 247.19 (M−1).

The amine was prepared using a similar procedure to the following:

A (Parr) pressure apparatus was charged with 3-amino-2-chloropyridine (500 mg, 3.89 mmol), 2-amino-5-chloropyridine (1.00 g, 7.78 mmol), palladium acetate (88 mg, 0.39 mmol), 1,3-bis(diphenylphosphino)propane (483 mg, 1.17 mmol) and triethylamine (590 mg, 5.84 mmol). The mixture was placed under a carbon monoxide atmosphere (4.1 bar) and heated at 100° C. After 72 h, the mixture was filtered, concentrated and the residue purified by column chromatography (SiO$_2$: 0 to 5% EtOAc in methylene chloride) affording 550 mg (57%) of the title compound.

$^1$H-NMR, IR

IS-MS, m/e 249 (M+1).

Analysis for C$_{11}$H$_9$ClN$_4$O: Calcd: C, 53.13; H, 3.65; N, 22.53; Found: C, 53.40; H, 3.66; N, 22.45.

Intermediate AA-14

3-Amino-N-(5-chloropyridin-2-yl)-6-methylpyridine-2-carboxamide.

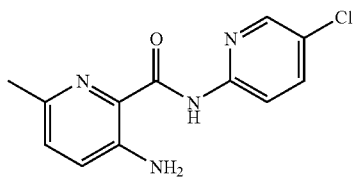

Using methods substantially equivalent to those described above for Intermediate AA-13, 3-amino-N-(5-chloropyridin-2-yl)-6-methylpyridine-2-carboxamide (16 g, 46%) was prepared from 3-amino-2-chloro-6-methylpyridine and 2-amino-5-chloropyridine.

$^1$H NMR

ESI-MS, m/e 263.1 (M+1).

Preparation of Intermediates A-1–A-5

The following intermediates were prepared by acylation of the requisite amine using 4-fluorobenzoyl chloride and a procedure similar to that described for the preparation of Intermediate A-2, or as otherwise described.

Intermediate A-1

5-Fluoro-2-(4-fluorobenzoylamino)-N-(5-chloropyridin-2-yl)-benzamide.

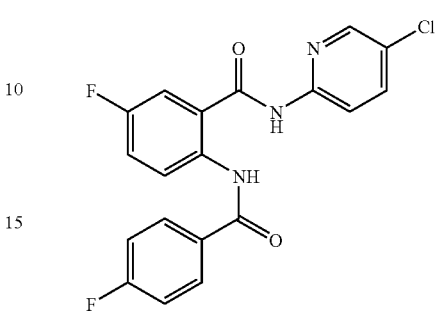

$^1$H-NMR (DMSO) δ 8.43 (d, J=2.6 Hz), 8.13 (d, J=9.0 Hz), 8.11 (d, J=9.0 Hz), 7.93–7.99 (m), 7.71 (dd, J=9.4 Hz and 3.0 Hz), 7.35–7.50 (m).

ESI-MS, m/e 388.09 (M+1).

Analysis for C$_{19}$H$_{12}$ClF$_2$N$_3$O$_2$: Calcd: C, 58.85; H, 3.12; N, 10.84; Found: C, 58.64; H, 3.16; N, 10.82.

Intermediate A-2

5-Chloro-2-(4-fluorobenzoylamino)-N-(5-chloropyridin-2-yl)-benzamide (General Procedure).

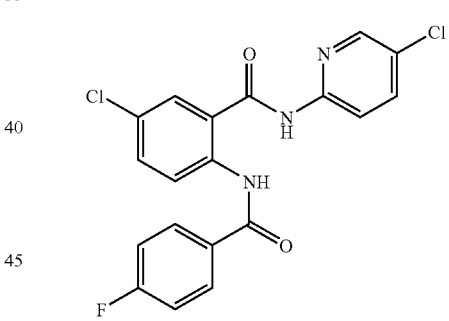

To a solution of 2-amino-5-chloro-N-(5-chloropyridin-2-yl)benzamide (2.82 g, 10 mmol) in methylene chloride (100 mL) and pyridine (3 mL) was added 4-fluorobenzoyl chloride (1.42 mL, 12 mmol) dropwise at 0° C. The reaction mixture was warmed to room temperature and stirred overnight. Water (50 mL) was added; and the mixture was stirred for 30 min before the solids were filtered, washed with saturated sodium bicarbonate (30 mL), water (30 mL), and ether (50 mL), and dried under vacuum to provide the product (3.2 g, 79%) pure enough to use in the next step.

$^1$H-NMR (DMSO, 250 MHz) δ 8.46 (d, J=2.1 Hz), 8.11–8.20 (m), 7.93–8.01 (m), 7.68 (dd, J=8.8 Hz and 2.4 Hz), 7.37–7.44 (m).

ESI-MS, m/e 402.17 (M−1).

Analysis for C$_{19}$H$_{12}$Cl$_2$FN$_3$O$_2$: Calcd: C, 56.46; H, 2.99; N, 10.40; Found: C, 55.97; H, 2.93; N, 10.43.

Intermediate A-3

5-Chloro-2-(4-fluorobenzoylamino)-N-(5-methylpyridin-2-yl)-benzamide.

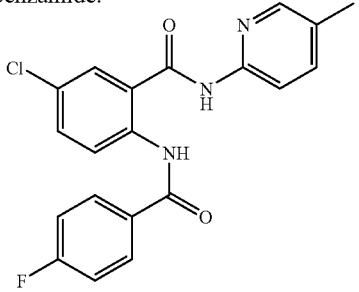

$^1$H-NMR (DMSO) δ 8.31 (d, J=9.14 Hz), 8.23 (d, J=1.8), 7.95–7.99 (m), 7.64–7.69 (m), 7.37–7.43 (m), 2.28 (s).
ESI-MS, m/e 384.21 (M+1).
Analysis for $C_{20}H_{15}ClFN_3O_2$: Calcd: C, 62.59; H, 3.94; N, 10.95; Found: C, 62.36; H, 4.04; N, 10.80.

Intermediate A-4

2-(4-Fluorobenzoylamino)-5-methyl-N-(5-methylpyridin-2-yl)-benzamide.

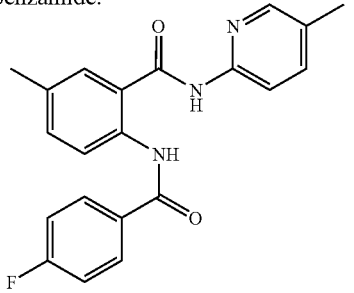

$^1$H-NMR (DMSO) δ 8.1 (d, J=8.1 Hz), 7.88–7.93 (m), 7.75 (s), 7.60 (d, J=8.4 Hz), 7.30–7.36 (m), 2.29 (s), 2.22 (s).
FD-MS, m/e 364.21 (M+1).
Analysis for $C_{21}H_{18}FN_3O_2$: Calcd: C, 69.41; H, 4.99; N, 11.56; Found: C, 69.03; H, 4.85; N, 11.51.

Intermediate A-5

3-(4-Fluorobenzoylamino)-N-(5-chloropyridin-2-yl)pyridine-2-carboxamide.

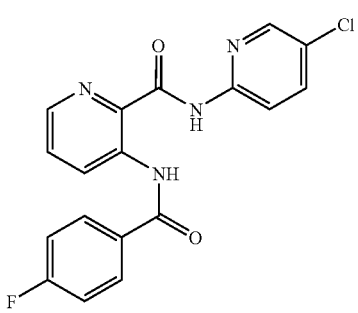

$^1$H-NMR (DMSO) δ 8.14 (dd, J=8.4 Hz and 1.5 Hz), 8.46 (d, J=2.9 Hz), 8.23 (d, J=8.8 Hz), 8.02–8.06 (m), 7.75–7.79 (2d, $J_1$=4.4 Hz, $J_2$=4.8 Hz), 7.44–7.50 (m), 7.29–7.35 (m)
ESI-MS, m/e 369.17 (M−1).
Analysis for $C_{18}H_{12}ClFN_4O_2$: Calcd: C, 58.31; H, 3.26; N, 15.11; Found: C, 57.82; H, 2.99; N, 14.95.

Preparation of Intermediates B-1–B-2

The following intermediates were prepared by acylation of the requisite amine using 4-fluoro-2-trifluoromethyl-benzoyl chloride and a procedure similar to that described for the preparation of Intermediate A-2, or as otherwise described.

Intermediate B-1

5-Fluoro-2-(4-fluoro-2-trifluoromethylbenzoylamino)-N-(5-chloropyridin-2-yl)benzamide.

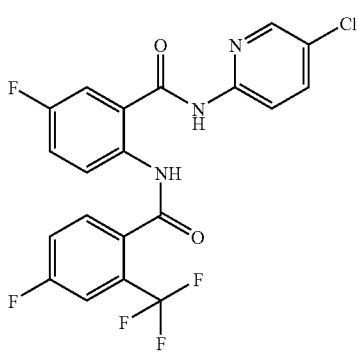

$^1$H-NMR (DMSO) δ 8.44 (d, J=2.3 Hz), 8.14 (d, J=8.7 Hz), 7.93 (dd, J=9.0 Hz and 2.6 Hz), 7.66–7.86 (m), 7.59 (dd, J=9.1 Hz and 2.8 Hz), 7.41–7.48 (m).
ESI-MS; m/e 456.20 (M+1).

Intermediate B-2

5-Chloro-2-(4-fluoro-2-trifluoromethylbenzoylamino)-N-(5-chloropyridin-2-yl)benzamide.

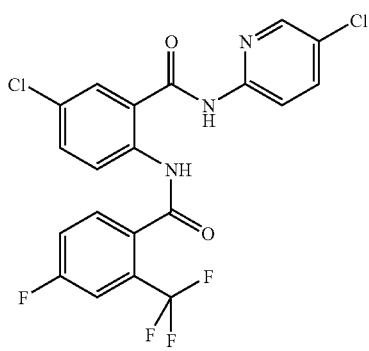

$^1$H-NMR (DMSO) δ 8.44 (d, J=2.3 Hz), 8.12 (d, J=9.0 Hz), 7.92 (dd, J=9.0 Hz and 2.6 Hz), 7.63–7.87 (m).
ESI-MS, m/e 472.14 (M+1).
Analysis for $C_{20}H_{11}Cl_2F_4N_3O_2$: Calcd: C, 50.87; H, 2.35; N, 8.90; Found: C, 50.58; H, 2.30; N, 8.61.

Preparation of Intermediates C-1–C-2

The following intermediates were prepared by acylation of the requisite amine using 4-fluoro-3-trifluoromethylbenzoyl chloride and a procedure similar to that described for the preparation of Intermediate A-2, or as otherwise described.

Intermediate C-1

5-Fluoro-2-(4-fluoro-3-trifluoromethylbenzoylamino)-N-(5-chloropyridin-2-yl)benzamide.

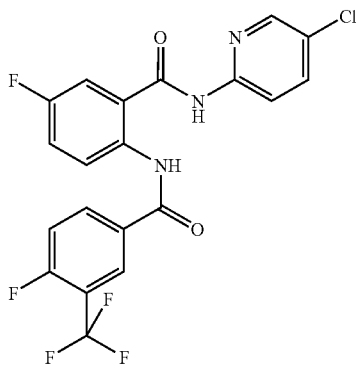

$^1$H-NMR (DMSO) δ 8.39 (d, J=2.6 Hz), 8.25 (dd, J=6.9 Hz and 2.6 Hz), 8.12 (d, J=8.7 Hz), 7.87–7.95 (m), 7.62–7.73 (m), 7.74–7.50 (m).

ESI-MS, m/e 456.19 (M+1).

Analysis for $C_{20}H_{11}ClF_5N_3O_2$: Calcd: C, 52.71; H, 2.43; N, 9.22; Found: C, 52.97; H, 2.33; N, 9.01.

Intermediate C-2

5-Chloro-2-(4-fluoro-3-trifluoromethylbenzoylamino)-N-(5-chloropyridin-2-yl)benzamide.

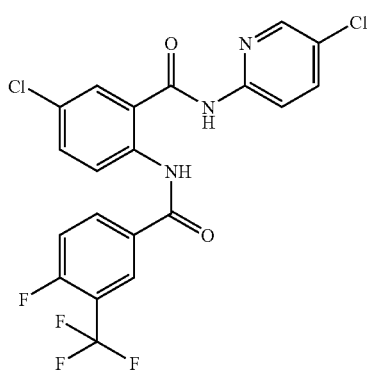

$^1$H-NMR (DMSO) δ 8.41 (d, J=2.6 Hz), 8.24 (d, J=6.8 Hz), 8.11 (d, J=9.0 Hz), 7.92–7.98 (m), 7.86 (d, J=2.3 Hz), 7.64–7.74 (m)

ESI-MS, m/e 472.11 (M+1).

Analysis for $C_{20}H_{11}Cl_2F_4N_3O_2$: Calcd: C, 50.87; H, 2.35; N, 8.90; Found: C, 51.02; H, 2.16; N, 8.69.

Preparation of Intermediate D-1

The following intermediate was prepared by acylation of the requisite amine using 3,4-difluorobenzoyl chloride and a procedure similar to that described for the preparation of Intermediate A-2, or as otherwise described.

Intermediate D-1

2-(3,14-Difluorobenzoylamino)-5-fluoro-N-(5-chloropyridin-2-yl)benzamide.

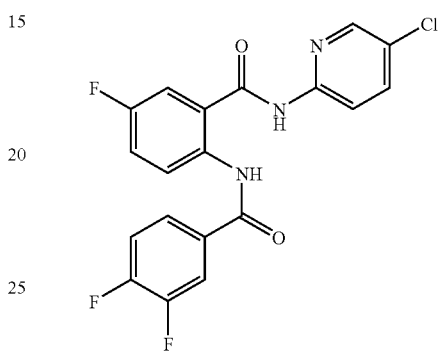

$^1$H-NMR (DMSO) δ 8.42 (d, J=2.6 Hz), 8.11 (d, J=9.0 Hz), 7.88–8.02 (m), 7.77 (s, br), 7.58–7.70 (m), 7.43–7.50 (m).

ESI-MS, m/e 406.35 (M+1).

Preparation of Intermediates E-1–E-2

The following intermediates were prepared by acylation of the requisite amine using 3,4,5-trifluorobenzoyl chloride and a procedure similar to that described for the preparation of Intermediate A-2, or as otherwise described.

Intermediate E-1

5-Fluoro-2-(3,4,5-trifluorobenzoylamino)-N-(5-chloropyridin-2-yl)benzamide.

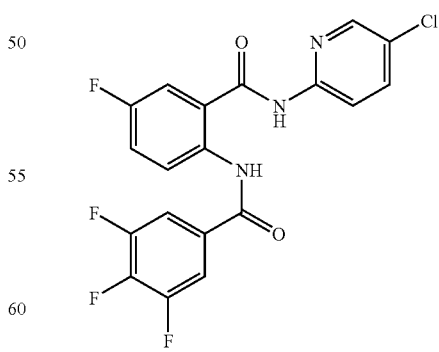

$^1$H-NMR (DMSO) δ 8.41 (d, J=2.6 Hz), 8.12 (d, J=9.0 Hz), 7.77–7.97 (m), 7.65 (dd, J=9.3 Hz and 2.8 Hz), 7.43–7.50 (m).

ESI-MS, m/e 423.99 (M+1).

Intermediate E-2

5-Chloro-2-(3,4,5-trifluorobenzoylamino)-N-(5-chloropyridin-2-yl)benzamide.

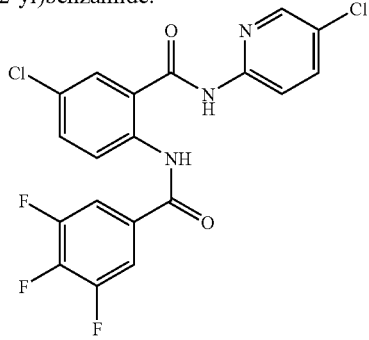

$^1$H-NMR (DMSO) δ 8.42 (d, J=2.3 Hz), 8.11 (d, J=9.0 Hz), 7.95 (dd, J=9.0 Hz and 2.2 Hz), 7.79–7.87 (m), 7.66 (dd, J=9.0 Hz and 2.3 Hz).

ESI-MS, m/e 440.01 (M+1).

Analysis for $C_{19}H_{10}Cl_2F_3N_3O_2$: Calcd: C, 51.84; H, 2.29; N, 9.55; Found: C, 52.08; H, 2.28; N, 9.41.

Preparation of Intermediate F-1

5-Fluoro-2-(4-fluoro-2-hydroxybenzoylamino)-N-(5-chloropyridin-2-yl)benzamide.

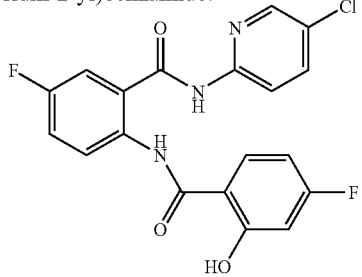

A. 5-Fluoro-2-(4-fluoro-2-acetoxybenzoylamino)-N-(5-chloropyridin-2-yl)benzamide.

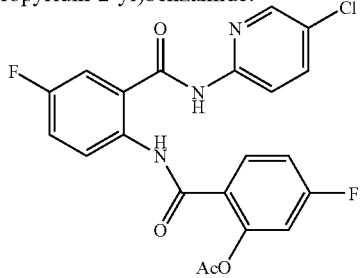

2-Amino-5-fluoro-N-(5-chloropyridin-2-yl)benzamide (5.32 g, 20 mmol) was added to a solution of 2 mL dry pyridine and 2-acetoxy-4-fluorobenzoyl chloride (21 mmol) in 100 mL dry methylene chloride under dry nitrogen with magnetic stirring. The reaction mixture was allowed to stir overnight at room temperature and then was diluted with 500 mL of methylene chloride. The methylene chloride solution was washed with cold 1 M HCl, cold saturated NaHCO$_3$, and brine; and then was dried over sodium sulfate. The solvent was evaporated, and the crude product was crystallized from acetone to give 2.92 g of off-white product.

$^1$H-NMR

ESI-MS, m/e 446.1 (M+1).

B. 5-Fluoro-2-(4-fluoro-2-hydroxybenzoylamino)-N-(5-chloropyridin-2-yl)benzamide.

The acetoxy compound from Part A above (2.75 g, 6 mmol) was dissolved in 75 mL of methanol under nitrogen. The solution was cooled in an ice-water bath and 0.5 M NaOH (13 mL, 6.5 mmol) was added. The reaction was stirred overnight while warming to room temperature. One molar HCl (6.5 mL, 6.5 mmol) was added. The mixture was diluted with additional water and the precipitated solid was filtered, washed with water, and dried over KOH in vacuo at 35° C. to give 2.15 g of the title product as a white solid (89% yield).

$^1$H-NMR

ESI-MS, m/e 404.4 (M+1).

Analysis for $C_{21}H_{14}ClF_2N_3O_4$: Calcd: C, 56.52; H, 3.00; N, 10.41; Found: C, 56.34; H, 2.93; N, 9.99.

Preparation of Intermediates F-2–F-6

The following intermediates were prepared by alkylation of 5-fluoro-2-(4-fluoro-2-hydroxybenzoylamino)-N-(5-chloropyridin-2-yl)benzamide (Intermediate F-1) using the described alkylating agent and a procedure similar to that described for the preparation of Intermediate F-2, or as otherwise described.

Intermediate F-2

5-Fluoro-2-(4-fluoro-2-ethoxybenzoylamino)-N-(5-chloropyridin-2-yl)-benzamide.

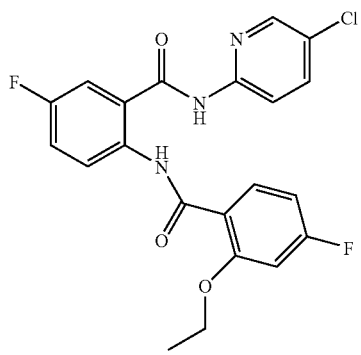

In a 4 mL screw cap vial fitted with a small egg-shaped stir bar, were combined 5-fluoro-2-(4-fluoro-2-hydroxybenzoylamino)-N-(5-chloropyridin-2-yl)benzamide (200 mg, 0.49 mmol) and powdered anhydrous K$_2$CO$_3$ (103 mg, 0.74 mmol, 1.5 eq) in 0.5 mL of dry dimethylformamide (DMF). Ethyl iodide (115 mg, 0.74 mmol) was then added, the vial was capped, and the slurry heated to 50° C. with vigorous stirring overnight. The slurry was diluted with 20 mL water and extracted into 15 mL of dichloromethane. The organic layer was then washed with 20 mL portions of saturated NaHCO$_3$, water, and brine; then dried over Na$_2$SO$_4$ and concentrated in vacuo. The residue was dissolved in a few mL of dichloromethane and purified by radial chromatography, eluting using hexanes, then 4:1 hexanes:EtOAc, to provide 135 mg (63%) of the title compound as pinkish-white crystals.

ES-MS, m/e 432.1 (M+1).

Intermediate F-3

5-Fluoro-2-(4-fluoro-2-isopropoxybenzoylamino)-N-(5-chloropyridin-2-yl)benzamide.

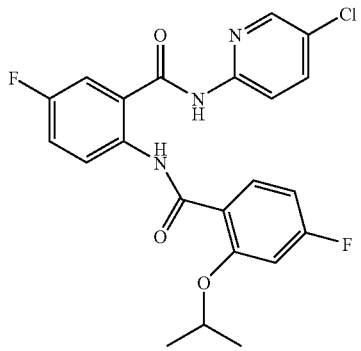

Prepared using 2-iodopropane.
ES-MS, m/e 446.1 (M+1).

Intermediate F-4

5-Fluoro-2-[4-fluoro-2-(2-hydroxyethoxy)benzoylamino]-N-(5-chloropyridin-2-yl)benzamide.

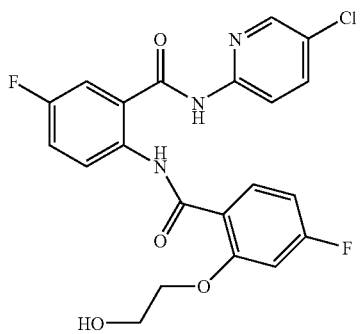

Prepared using 2-bromoethanol and the addition of a few mg of tetrabutylammonium iodide and heating for 48 hours at 75° C. instead of 36–40 hours at 50° C.
ES-MS, m/e 448.0 (M+1).

Intermediate F-5

5-Fluoro-2-[4-fluoro-2-(2-methoxyethoxy)benzoylamino]-N-(5-chloropyridin-2-yl)benzamide.

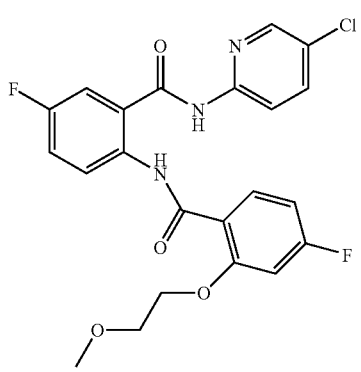

Prepared (46% yield) using 2-bromoethyl methyl ether and the tetrabutylammonium iodide and conditions as described for Intermediate F-4.
ES-MS, m/e 462.1 (M+1).

Intermediate F-6

5-Fluoro-2-[4-fluoro-2-(2-methylthioethoxy)benzoylamino]-N-(5-chloropyridin-2-yl)benzamide.

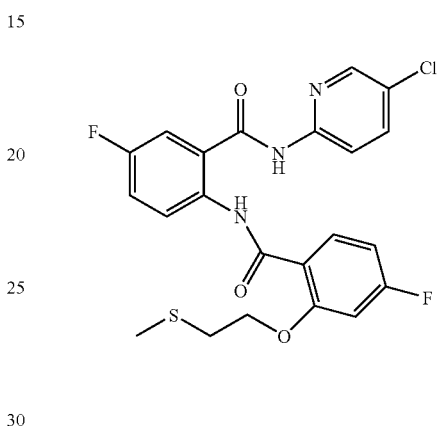

In a flame-dried 50 mL round bottomed single necked flask were combined 5-fluoro-2-(4-fluoro-2-hydroxybenzoylamino)-N-(5-chloropyridin-2-yl)benzamide (491 mg, 1.22 mmol), 2-(methylthio)ethanol (160 µL, 168 mg, 1.82 mmol, 1.5 eq), and triphenylphosphine (477 mg, 1.82 mmol) under a nitrogen atmosphere in 30 mL of dry tetrahydrofuran (THF) to produce a milky-white slurry. Diisopropyl azodicarboxylate (DIAD, 358 µL, 368 mg, 1.82 mmol) was then added dropwise via syringe over 10–15 min to the stirring slurry. The milky-white slurry changed to a clear light orange-yellow solution during DIAD addition and this solution was stirred overnight under nitrogen at room temperature. The reaction mixture was concentrated in vacuo and the resulting orange oil was dissolved in ethyl acetate (100 mL), washed with water and brine, then dried over sodium sulfate and concentrated again to yield an orange oil. The oil was purified on a 75 mL column of silica gel using a step gradient of 100:0, 95:5, 9:1, 85:15 and 8:2 hexanes:EtOAc, then by radial chromatography with 9:1 and 8:2 hexanes:EtOAc and finally by recrystallization from 9:1 hexanes:EtOAc to produce 213 mg (37%) of the title compound as white needles.
$^1$H-NMR
ESI-MS, m/e 478.1 (M+1)

PREPARATION OF EXAMPLES P1–P3

The following protected examples were prepared using 1-t-butoxycarbonylhexahydro-1,4-diazepine and the requisite intermediate and a procedure similar to that described for the preparation of Example 5, or as otherwise described.

EXAMPLE P1

2-[4-(4-t-Butoxycarbonylhexahydro-1,4-diazepin-1-yl)benzoylamino]-5-fluoro-N-(5-chloropyridin-2-yl)benzamide.

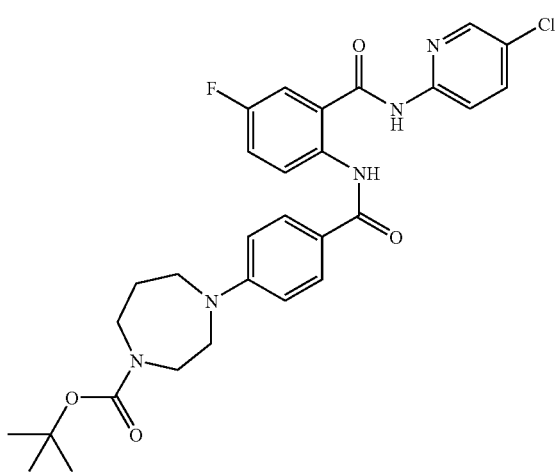

Directly Deprotected without Obtaining Spectra.

EXAMPLE P2

2-[4-(4-t-Butoxycarbonylhexahydro-1,4-diazepin-1-yl)benzoylamino]-5-chloro-N-(5-chloropyridin-2-yl)benzamide.

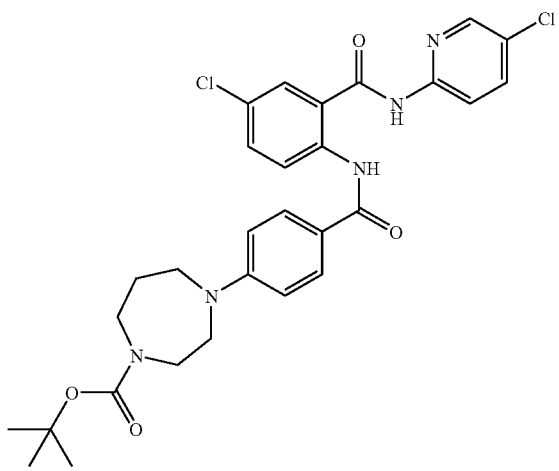

Directly Deprotected without Obtaining Opectra.)

EXAMPLE P3

2-[4-(4-t-Butoxycarbonylhexahydro-1,4-diazepin-1-yl)benzoylamino]-5-methyl-N-(5-methylpyridin-2-yl)benzamide.

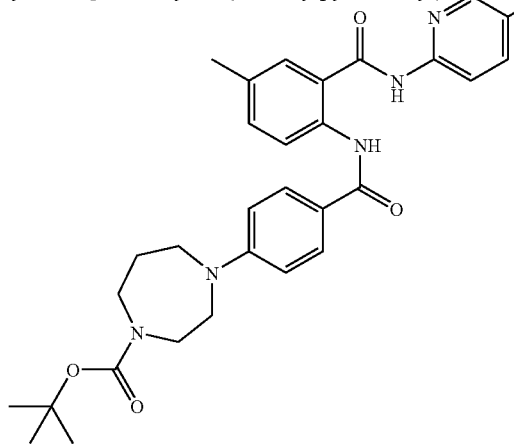

Directly Deprotected without Obtaining Spectra.

PREPARATION OF EXAMPLES 1–3

The following examples were prepared using the requisite 1-t-butoxycarbonyl protected hexahydro-1,4-diazepine described above and a procedure similar to that described for the preparation of Example 1, or as otherwise described.

Preparation of Salts

TFA salts were obtained by removal of the solvent after the deprotection of nitrogen in methylene chloride and TFA.

Monohydrochlorides were prepared by treating the free bases suspended in methylene chloride, methanol mixture (4:1) with one equivalent of HCl in ether and sonicating for five minutes and evaporating off the solvent.

Similarly the polyhydrochlorides were prepared by treatment with excess HCl in ether.

EXAMPLE 1

5-Fluoro-2-[4-(hexahydro-1,4-diazepin-1-yl)benzoylamino]-N-(5-chloropyridin-2-yl)benzamide.

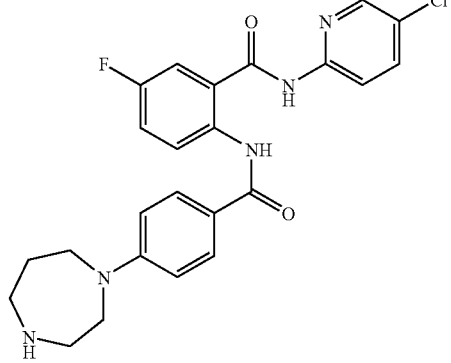

To a suspension of 2-[4-(4-t-butoxycarbonylhexahydro-1,4-diazepin-1-yl)benzoylamino]-5-fluoro-N-(5-chloropyridin-2-yl)benzamide (Example P1, 0.59 g) in methylene chloride (3 mL) and anisole (1 mL) was added trifluoroacetic acid (3 mL) dropwise. The mixture was stirred overnight at room temperature before the solvent was evaporated. The residue was purified by using an SCX column. Yield 0.337 g.

¹H-NMR
ESI-MS, m/e 468.20 (M+1)

EXAMPLE 2

5-Chloro-2-[4-(hexahydro-1,4-diazepin-1-yl)benzoylamino]-N-(5-chloropyridin-2-yl)benzamide.

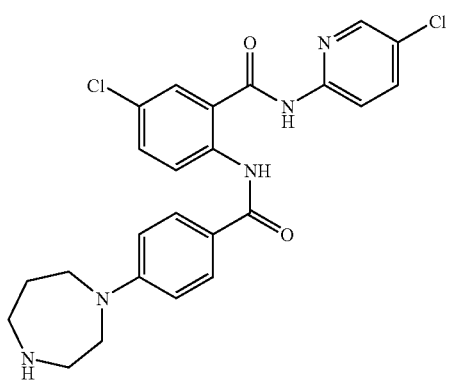

¹H-NMR
ESI-MS, m/e 484.41 (M+1).

EXAMPLE 3a

2-[4-(Hexahydro-1,4-diazepin-1-yl)benzoylamino]-5-methyl-N-(5-methylpyridin-2-yl)benzamide.

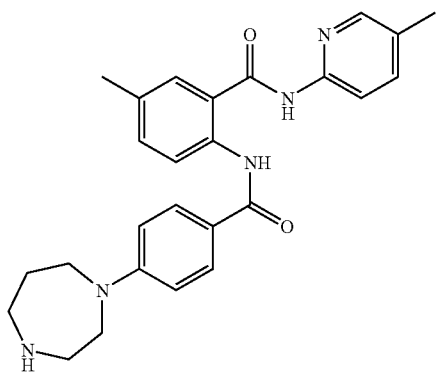

¹H-NMR
ESI-MS, m/e 444.2 (M+1).

EXAMPLE 3b

2-[4-(Hexahydro-1,4-diazepin-1-yl)benzoylamino]-5-methyl-N-(5-methylpyridin-2-yl)benzamide Hydrochloride Hydrate.

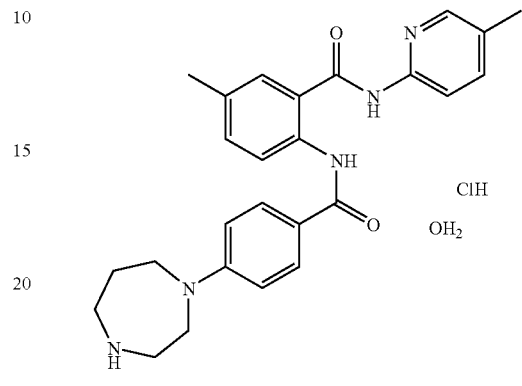

¹H-NMR
ESI-MS, m/e 444.19(M+1).

PREPARATION OF EXAMPLES 4–15

The following examples having a substituent on the 4-position of the hexahydro-1,4-diazepin-1-yl moiety were prepared from the corresponding 1-substituted hexahydro-1,4-diazepine and the requisite intermediate by using a procedure similar to that described for the preparation of Example 5, or as otherwise described.

EXAMPLE 4

5-Fluoro-2-[4-(4-methylhexahydro-1,4-diazepin-1-yl)benzoylamino]-N-(5-chloropyridin-2-yl)benzamide.

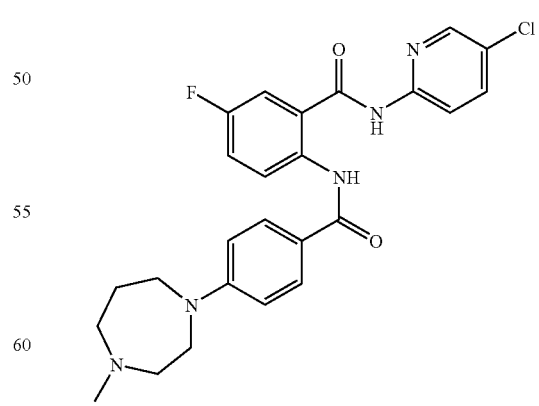

¹H-NMR
ESI-MS, m/e 482.33 (M+1).

EXAMPLE 5

5-Chloro-2-[4-(4-methylhexahydro-1,4-diazepin-1-yl)benzoylamino]-N-(5-chloropyridin-2-yl)benzamide.

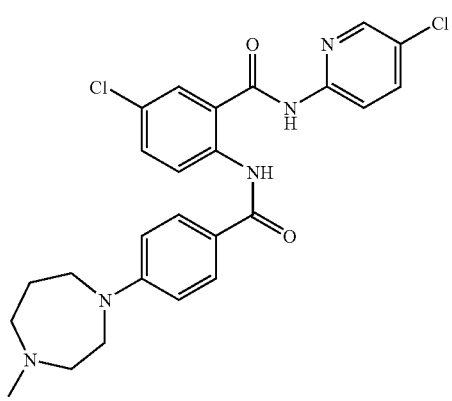

General Procedure

A mixture of 5-chloro-2-[4-fluorobenzoylamino]-N-(5-chloropyridin-2-yl)benzamide (Intermediate A-2, 0.4042 g, 1 mmol), 1-methyl-hexahydro-1,4-diazepine (0.37 mL, 3 mmol), dimethyl sulfoxide (3 mL) in a sealed tube was heated at 90° C. for 24 h in an oil bath. The mixture was cooled to room temperature and partitioned between ethyl acetate (200 mL) and saturated sodium bicarbonate (50 mL). After the the aqueous layer was extracted with ethyl acetate (50 mL), the organic layers were combined, washed with saturated sodium bicarbonate (50 mL) and water (50 mL), dried (MgSO$_4$) and evaporated under vacuum. The residue was purified by column chromatography over silica gel, eluting with methylene chloride:[2 M ammonia in methanol] (19:1), to give pure product (0.237 g, 48%).

$^1$H-NMR

ESI-MS, m/e 498.23 (M+1).

EXAMPLE 6

5-Chloro-2-[4-(4-methylhexahydro-1,4-diazepin-1-yl)benzoylamino]-N-(5-methylpyridin-2-yl)benzamide.

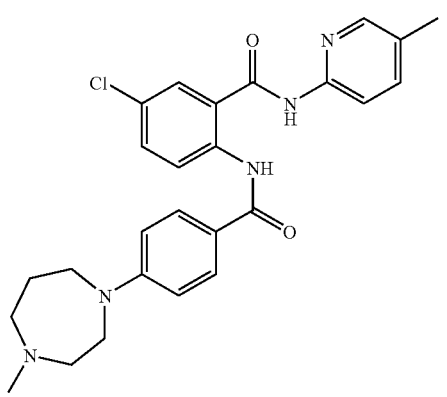

$^1$H-NMR

ESI-MS, m/e 478.24 (M+1).

EXAMPLE 7

5-Nethyl-2-[4-(4-methylhexahydro-1,4-diazepin-1-yl)benzoylamino]-N-(5-methylpyridin-2-yl)benzamide.

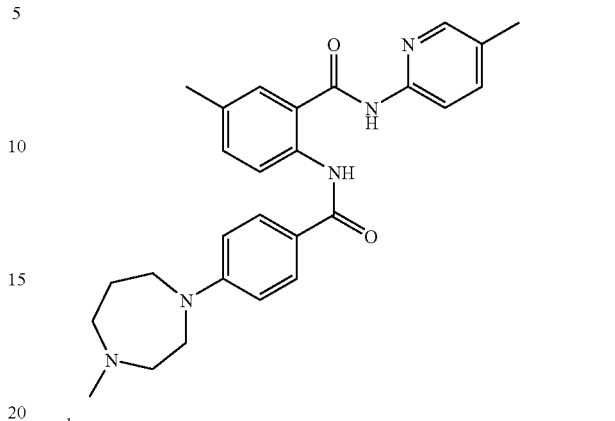

$^1$H-NMR

ESI-MS, m/e 458.48 (M+1).

Analysis for C$_{27}$H$_{31}$N$_5$O$_2$: Calcd: C, 70.87; H, 6.83; N, 15.31; Found: C, 70.61; H, 6.94; N, 15.10.

EXAMPLE 8

3-[4-(4-Methylhexahydro-1,4-diazepin-1-yl)benzoylamino]-N-(5-chloropyridin-2-yl)pyridine-2-carboxamide.

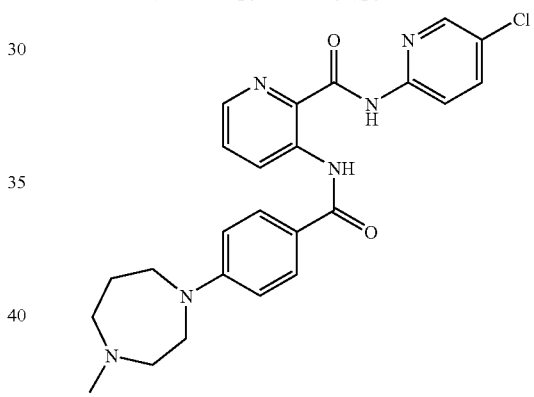

$^1$H-NMR

ESI-MS, m/e 465.20 (M+1).

EXAMPLE 9

5-Fluoro-2-[4-(4-methylhexahydro-1,4-diazepin-1-yl)-2-trifluoromethylbenzoylamino]-N-(5-chloropyridin-2-yl)-benzamide.

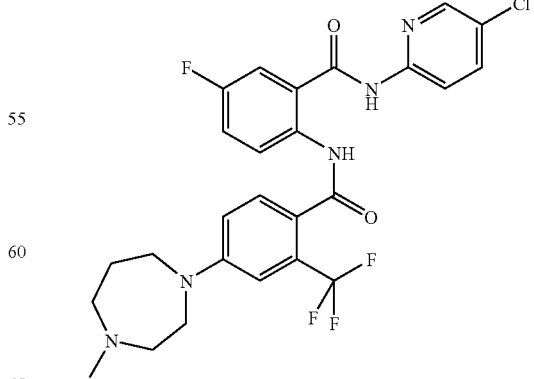

$^1$H-NMR

ESI-MS, m/e 550.24 (M+1).

EXAMPLE 10

5-Chloro-2-[4-(4-methylhexahydro-1,4-diazepin-1-yl)-2-trifluoromethylbenzoylamino]-N-(5-chloropyridin-2-yl)-benzamide.

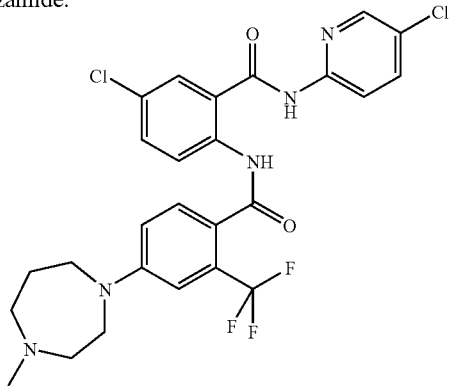

$^1$H-NMR
ESI-MS, m/e 566.49 (M+1).

EXAMPLE 11

5-Fluoro-2-[4-(4-methylhexahydro-1,4-diazepin-1-yl)-3-trifluoromethylbenzoylamino]-N-(5-chloropyridin-2-yl)-benzamide.

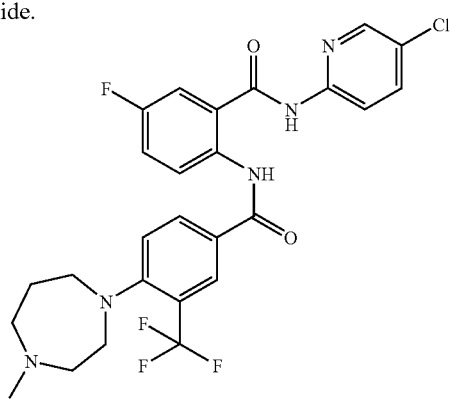

$^1$H-NMR
ESI-MS, m/e 550.25 (M+1)

EXAMPLE 12

5-Chloro-2-[4-(4-methylhexahydro-1,4-diazepin-1-yl)-3-trifluoromethylbenzoylamino]-N-(5-chloropyridin-2-yl)-benzamide.

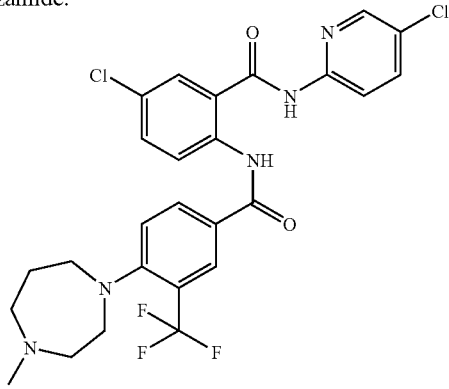

$^1$H-NMR
ESI-MS, m/e 566.47 (M+1).

EXAMPLE 13

5-Fluoro-2-[3-fluoro-4-(4-methylhexahydro-1,4-diazepin-1-yl)benzoylamino-N-(5-chloropyridin-2-yl)benzamide.

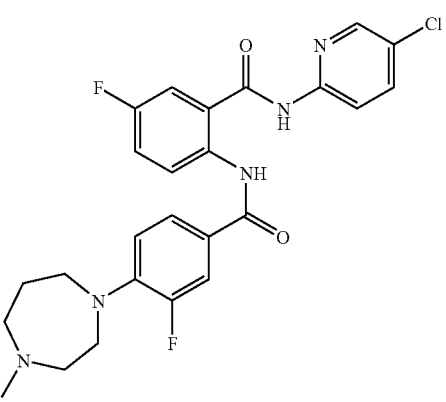

$^1$H-NMR
FD-MS m/e 499.25 (M+).

EXAMPLE 14

2-[3,5-Difluoro-4-(4-methylhexahydro-1,4-diazepin-1-yl)-benzoylamino]-5-fluoro-N-(5-chloropyridin-2-yl)benzamide.

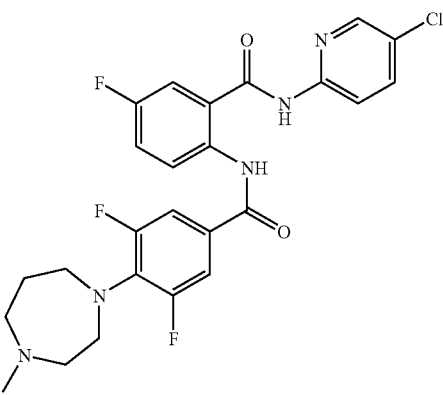

$^1$H-NMR
ESI-MS, m/e 518.25 (M+1).
Analysis for $C_{25}H_{23}ClF_3N_5O_2$: Calcd: C, 57.98; H, 4.48; N, 13.52; Found: C, 57.68; H, 4.76; N, 13.26.

EXAMPLE 15

5-Chloro-2-[3,5-difluoro-4-(4-methylhexahydro-1,4-diazepin-1-yl)benzoylamino]-N-(5-chloropyridin-2-yl)benzamide.

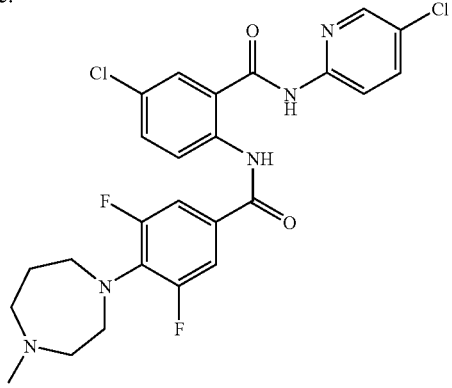

¹H-NMR
ESI-MS, m/e 534.17 (M+1).

EXAMPLE 16

Preparation of 2-[4-(4-Methylhexahydro-1,4-diazepin-1-yl)-benzylamino]-N-(5-chloropyridin-2-yl)pyridine-3-carboxamide.

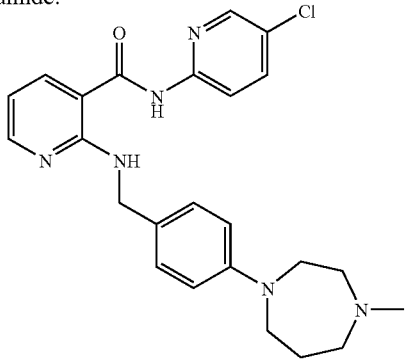

A. 4-Fluorobenzamide.

A solution of 4.03 g (3.0 mL) of 4-fluorobenzoyl chloride was added dropwise to 100 mL 0.5 M NH₃/dioxane. After 4.5 h, this reaction mixture was evaporated to dryness, dissolved in chloroform, washed with aqueous sodium bicarbonate, washed with water, filtered, and evaporated to give the amide (2.81, 80%).
¹H-NMR
IS-MS, m/e=140 (M+1).

B. 4-(4-Methylhexahydro-1,4-diazepin-1-yl)benzamide.

4-Fluorobenzamide (2.8 g, 20.1 mmol) in 1-methylhexahydro-1,4-diazepine (10 mL, 80.4 mmol) was heated at 130° C. for 28.5 h. The reaction mixture was diluted with 400 mL of water, the insoluble solid was filtered and washed with water. This solid was redissolved in methanol, filtered and evaporated to give 2.1 g (46%) of crude substituted benzamide.
IS-MS, m/e=234 (M+1).

C. 4-(4-Methylhexahydro-1,4-diazepin-1-yl)benzylamine.

4-(4-Methylhexahydro-1,4-diazepin-1-yl)benzamide (2.1 g, 9.2 mmol) was suspended in 100 mL of dry THF and treated portionwise with lithium aluminum hydride (0.5 g, 12.5 mmol) at room temperature. After the gas evolution ceased, the reaction mixture was refluxed for 21.5 hours. The cooled mixture was diluted with 50 mL of THF and treated dropwise with 0.5 mL of water and 0.5 mL of 5 N NaOH, respectively. This mixture was refluxed for 0.5 hour, filtered through diatomaceous earth, and the filtrate was evaporated to give 1.9 g crude amine. Flash chromatography purification with 10% MeOH—CHCl₃, 1% NH₄OH gave the desired product (0.89 g, 44%).
¹H-NMR
IS-MS, m/e=220 (M+1).

D. 2-[4-(4-Methylhexahydro-1,4-diazepin-1-yl)benzylamino]-N-(5-chloropyridin-2-yl)pyridine-3-carboxamide.

A mixture of 2-chloro-N-(5-chloropyridin-2-yl)pyridine-3-carboxamide (1.00 g, 3.7 mmol) and 4-(4-methylhexahydro-1,4-diazepin-1-yl)benzylamine (0.63 g, 2.9 mmol), in 5 mL of DMSO, was heated in a sealed tube at 70–75° C. for 35 h. This reaction mixture was diluted with 250 mL of water, basified with 2 N NaOH, and extracted with ethyl acetate and evaporated to give 0.83 g crude product. Flash chromatography purification with 10% MeOH—CHCl₃, 1% NH₄OH gave the title product (0.11 g, 8.5%).
¹NMR (300 MHz, CDCl₃) δ: 8.35 (d, J=8.8 Hz, 2H); 8.24 (m, 1H); 8.21 (d, J=8.8 Hz, 1H); 7.76 (dd, J=1.5, 6.2 1H); 7.67 (dd, 2.6, 6.2 Hz, 1H); 7.24 (d, 2H); 6.66 (d, J=8.4 Hz, 2H); 6.58 (m, 1H); 4.61 (d, J=4.8 Hz); 3.58 (m, 2H); 3.47 (m, 2H); 2.72 (bs, 2H); 2.58 (bs, 2H); 2.39 (s, 3H); 2.20 (bs, 2H).
IS-MS, m/e=451.2 (M+1).

The 2-chloro-N-(5-chloropyridin-2-yl)pyridine-3-carboxamide for the above step was prepared by dropwise addition of 2-chloronicotinoyl chloride to an ice cooled solution of 2-amino-5-chloropyridine and pyridine in dichloromethane. The reaction mixture was allowed to warm to room temperature and stir a number of hours (overnight) before it was evaporated and the residue partitioned between ethyl acetate and water. The aqueous layer was extracted with ethyl acetate and the combined organic layers were washed with water, saturated citric acid solution, saturated sodium bicarbonate solution and water. After drying over magnesium sulfate and evaporation, the residue was slurried with ether and collected by filtration.

EXAMPLE 17

Preparation of 5-Chloro-2-[2-hydroxy-4-(4-methylhexahydro-1,4-diazepin-1-yl)benzoylamino]-N-(5-chloropyridin-2-yl)-benzamide Tris(trifluoroacetic Acid) Salt.

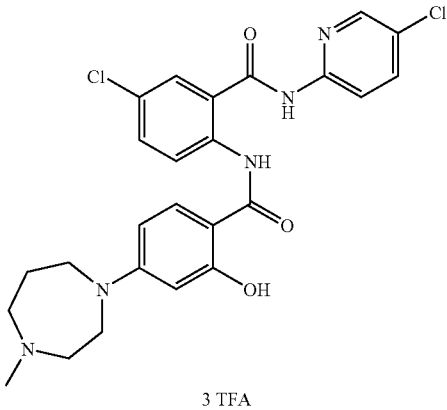

2-Methoxymethyl-4-(4-methylhexahydro-1,4-diazepin-1-yl)benzoyl chloride (1.73 g) was dissolved in DMF (15 mL) and added to a DMF (20 mL) solution of 2-amino-5- chloro-N-(5-chloropyridin-2-yl)benzamide (1.27 g, 4.5 mmol) cooled in an ice bath. The mixture was allowed to warm slowly to room temperature, and after 16 h was filtered, partitioned between EtOAc (200 mL) and satd NaHCO$_3$ (200 mL). The organic layer was washed with NaHCO$_3$ (200 mL×2), dried (MgSO$_4$), and evaporated. Crystalline intermediate O-protected bis-amide (507 mg) was obtained from concentrated methylene chloride-hexane.

$^1$H-NMR (CDCl$_3$) δ: 1.85(m,2H), 2.22(s,3H), 2.40 (m,2H), 2.57(m,2H), 3.31(s,3H), 3.44(m,2H), 3.52(m, 2H), 5.41(s,2H), 6.40(s,1H), 6.46(d,2H), 7.55(d,1H), 7.76(s,1H), 7.82(d,1H), 7.98(d,1H), 8.16(d,1H), 8.43(s, 1H), 8.55(d, 1H), 11.26(s,1H), 11.32(s,1H);

ESI-MS, m/e 558 (M+1).

The O-protected bis-amide (403 mg) was dissolved in 20 mL TFA. To the solution was added 20 mL water. The reaction mixture was stirred 2 h, evaporated, and triturated with ether-hexane, to give the title compound (0.39 g) as a crystalline solid.

$^1$H-NMR (DMSOd$_6$) δ: 2.10(m,2H), 2.80(s,3H), 2.80(m, 1H), 3.15(m,2H), 3.45(m,2H), 3.80(m,2H), 6.17(s,1H), 6.41 (d,1H), 7.57(d,1H), 7.70(d,1H), 7.79(s,1H) 7.96(d,1H), 8.08 (d,1H), 8.26(d,1H), 8.42(s,1H), 11.15(s,1H), 11.21(s,1H), 11.69(s,1H)

ESI-MS, m/e 514 (M+1).

The starting material acid chloride was prepared as follows.

A. Methyl 2-Methoxymethyl-4-fluorobenzoate.

Into a DMF (200 mL) solution of methyl 4-fluoro-2-hydroxybenzoate (17.0 g, 100 mL), cooled in an ice bath, was added K$_2$CO$_3$ (27.6 g, 200 mmol) and chloromethymethyl ether (9.11 mL, 120 mmol) dropwise. The reaction mixture was allowed to come to room temperature slowly and was stirred 48 h. To the reaction mixture at room temperature was added additional K$_2$CO$_3$ (6.9 g, 50 mmol) and chloromethylmethyl ether (4.5 mL, 60 mmol), and stirring was continued for 24 h. Most of the solvent was evporated in a bath at 60° C., and the residue was partitioned between ether (250 mL) and water (250 mL). The organic layer was washed with 1 N HCl (200 mL), dried (MgSO$_4$), and evaporated. The crude product was chromatographed over silica (eluting with 0 to 20% EtOAc in hexane gradient), giving 11.38 g (57% yield) of the named product as an oil.

$^1$H-NMR (CDCl$_3$) δ: 3.86(s,3H), 5.23(s,2H), 6.72(m,1H), 6.93(m,1H), 7.82(m, 1H)

B. Methyl 2-Methoxymethyl-4-(4-methylhexahydro-1,4-diazepin-1-yl)benzoate.

Into DMSO (5 mL) was dissolved the 4-fluorobenzoate from the above Part A (2.0 g, 10.1 mmol) and 1-methylhexahydro-1,4-diazepine (6.28 mL, 50.5 mmol). The mixture was heated 14 h at 98° C. before it was partitioned brine (300 mL) and EtOAc (300 mL). The organic layer was washed with brine (300 mL×2), dried (MgSO$_4$), and evaporated, giving the named compound (1.63 g, 52%) as an oil. The product was used in the next step without further purification.

$^1$H-NMR (CDCl$_3$) δ: 2.05(m,2H), 2.40(s,3H), 2.60(m, 1H), 2.73(m,1H), 3.50(m,1H), 3.51(s,3H), 3.61(m, 1H), 3.80(s, 3H), 5.22(s,2H), 6.31(d,1H), 6.41(s,1H), 7.75(d, 1H)

C. 2-Methoxymethyl-4-(4-methylhexahydro-1,4-diazepin-1-yl)benzoyl Chloride.

Into 15 mL THF was dissolved the ester from Part B above (5.29 mmol), followed by LiOH.H$_2$O (0.488 g, 11.6 mmol) in 5 mL water. The mixture was heated 24 h at 65° C., evaporated, and then evaporated twice from toluene (50 mL), giving the lithium benzoate.

The lithium benzoate was suspended in 50 mL methylene chloride in ice bath. To the suspension was added DMF (5 drops), pyridine (4.28 mL, 53 mmol), and oxalyl chloride (1.02 mL, 11.6 mmol). After the reaction mixture had stirred 30 min, the ice bath was removed and stirring continued for 30 min. The reaction mixture was evaporated in a bath at 35° C., giving 1.73 g of crude acid chloride.

PREPARATION OF EXAMPLES 18–22

The following examples were prepared using 1-methylhexahydro-1,4-diazepine and the requisite Intermediate F-2–F-6 described above and a procedure similar to that described for the preparation of Example 18a, or as otherwise described.

Trihydrochloride salts were prepared as described for Example 19b, or as otherwise described.

EXAMPLE 18a

2-[2-Ethoxy-4-(4-methylhexahydro-1,4-diazepin-1-yl)benzoylamino]-5-fluoro-N-(5-chloropyridin-2-yl)benzamide.

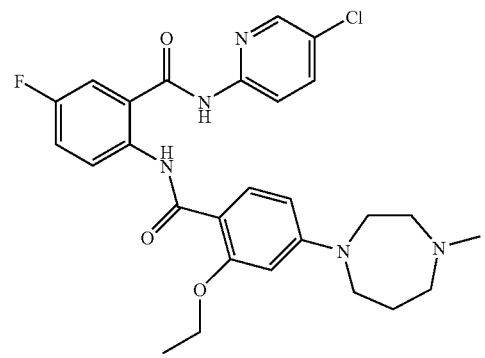

5-Fluoro-2-[4-fluoro-2-ethoxybenzoylamino]-N-(5-chloropyridin-2-yl)benzamide (135 mg, 0.31 mmol) and 1-methylhexahydro-1,4-diazepine (177 mg, 1.55 mmol, 5 eq) were dissolved in 250 µL DMSO, in a 4 mL screw cap vial. The pale yellow solution was incubated at 100° C. for 36–40 hours. The solution was cooled, diluted with 12 mL of dichloromethane, washed four times with water, once with brine, then dried over sodium sulfate and concentrated in vacuo. The crude residue was purified first by chromatography on a silica gel cartridge (2 g/12 cc, Varian Sample Preparation Products, Harbor City, Calif.) using zero to ten percent methanol in dichloromethane, then by radial chromatography with zero to ten percent methanol in dichloromethane. Pure fractions were pooled, concentrated in vacuo and dried under high vacuum to yield 107 mg (65%) of the title compound.

ES-MS, m/e 526.1 (M+1).

EXAMPLE 18b

2-[2-Ethoxy-4-(4-methylhexahydro-1,4-diazepin-1-yl)benzoylamino]-5-fluoro-N-(5-chloropyridin-2-yl)benzamide Trihydrochloride.

100 mg (82%) was prepared from its free base.

EXAMPLE 19a

5-Fluoro-2-[2-isopropoxy-4-(4-methylhexahydro-1,4-diazepin-1-yl)benzoylamino]-N-(5-chloropyridin-2-yl)benzamide.

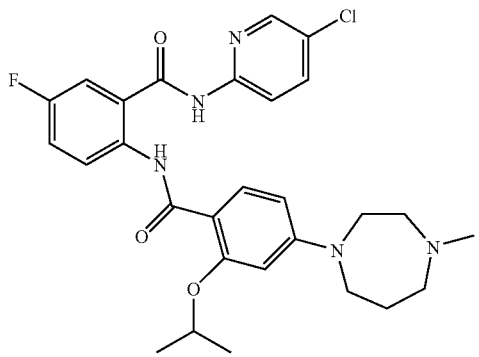

Prepared from 5-fluoro-2-(4-fluoro-2-isopropoxybenzoylamino)-N-(5-chloropyridin-2-yl)benzamide (159 mg, 0.356 mmol) and 1-methyl-hexahydro-1,4-diazepine (203 mg, 1.77 mmol, 5 eq) to provide 192 mg (82%) of the title compound.
ES-MS, m/e 540.2 (M+1).

EXAMPLE 19b

5-Fluoro-2-[2-isopropoxy-4-(4-methylhexahydro-1,4-diazepin-1-yl)benzoylamino]-N-(5-chloropyridin-2-yl)benzamide Trihydrochloride.

To 5-fluoro-2-[2-isopropoxy-4-(4-methylhexahydro-1,4-diazepin-1-yl)benzoylamino]-N-(5-chloropyridin-2-yl)-benzamide (150 mg, 0.278 mmol) suspended in 5 mL of 1:1 acetonitrile:water was added 1 mL of 1.0 N HCl solution (1 mmol, 3.6 eq), and the mixture was mixed to yield a clear light yellow solution. A portion of the solution was reserved for HPLC analysis. The remaining solution was frozen on dry ice, then lyophilized to produce 140 mg (78%) of the title trihydrochloride as a fluffy light yellow powder.

EXAMPLE 20a

5-Fluoro-2-[2-(2-hydroxyethoxy)-4-(4-methylhexahydro-1,4-diazepin-1-yl)benzoylamino]-N-(5-chloropyridin-2-yl)-benzamide.

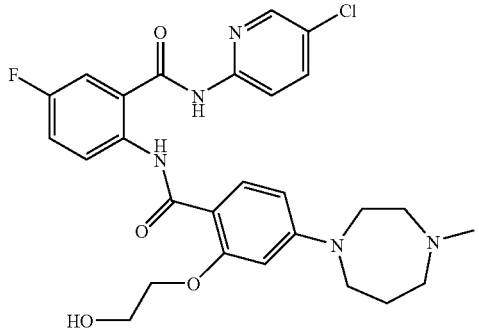

Prepared from 5-fluoro-2-[4-fluoro-2-(2-hydroxyethoxy)-benzoylamino]-N-(5-chloropyridin-2-yl)-benzamide and 1-methyl-hexahydro-1,4-diazepine to afford 25 mg (24%).
ES-MS, m/e 542.1 (M+1).

EXAMPLE 20b

5-Fluoro-2-[2-(2-hydroxyethoxy)-4-(4-methylhexahydro-1,4-diazepin-1-yl) benzoylamino]-N-(5-chloropyridin-2-yl)-benzamide-diazepin-2-yl)-benzamide Trihydrochloride.
8 mg (35%) was prepared from its free base.

EXAMPLE 21a

5-Fluoro-2-[2-(2-methoxyethoxy)-4-(4-methylhexahydro-1,4-diazepin-1-yl)benzoylamino]-N-(5-chloropyridin-2-yl)-benzamide.

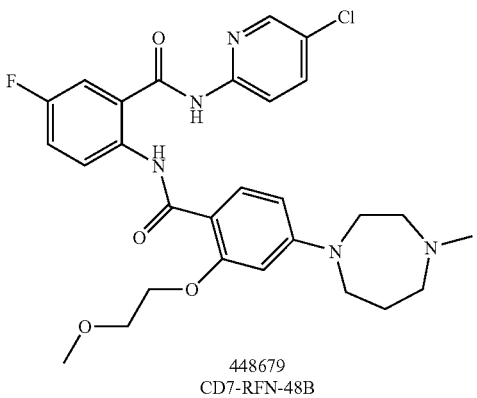

448679
CD7-RFN-48B

Prepared from 5-fluoro-2-[4-fluoro-2-(2-methoxyethoxy)-benzoylamino]-N-(5-chloropyridin-2-yl)-benzamide and 1-methyl-hexahydro-1,4-diazepine to afford 91 mg (72%).
ES-MS, m/e 556.2 (M+1).

EXAMPLE 21b

5-Fluoro-2-[2–4(2-methoxyethoxy)-4-(4-methylhexahydro-1,4-diazepin-1-yl)-b nzoylamino]-N-(5-chloropyridin-2-yl)-benzamide Trihydrochloride.
75 mg (73%) was prepared from its free base.

EXAMPLE 22

5-Fluoro-2-[4-(4-methylhexahydro-1,4-diazepin-1-yl)-2-(2-methylthioethoxy)benzoylamino]-N-(5-chloropyridin-2-yl) benzamide.

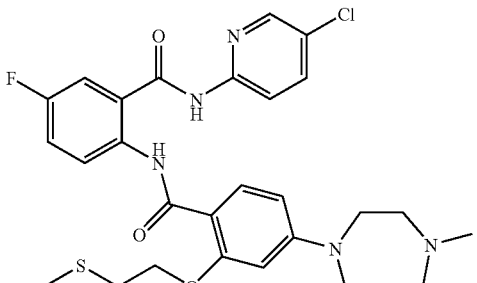

In a 4 mL screw-cap vial were dissolved 5-fluoro-2-[4-fluoro-2-(2-methylthioethoxy)benzoylamino]-N-(5-chloropyridin-2-yl)benzamide (131 mg, 274 µmol) and 1-methyl-hexahydro-1,4-diazepine (157 mg, 1.37 mmol, 5 eq) in 250 µL DMSO to give a light yellow solution. The solution was heated to 100° C. for 36 hours in a heatblock, then allowed to cool to room temperature. The resulting brown solution was diluted with 1 mL dichloromethane, washed four times with water, once with brine, then dried over sodium sulfate and concentrated. The residue was combined with that from a separate, smaller scale run (100 μmol of starting benzamide) and purified via radial chromatography with 95:5, then 9:1 dichloromethane:methanol to produce 184 mg (86%) of the title compound as a yellow oil.

¹H-NMR

ES-MS, m/e 572.2 (M+1).

Analysis for $C_{28}H_{31}ClFN_5O_3S$: Calcd: C, 58.78; H, 5.46; N, 12.24; Found: C, 58.29; H, 5.54; N, 12.05.

EXAMPLE 23

Preparation of 5-Chloro-2-[4-(4-methylhexahydro-1,4-diazepin-1-yl)cyclohexylcarbonylamino]-N-(5-chloropyridin-2-yl)benzamide Dihydrochloride.

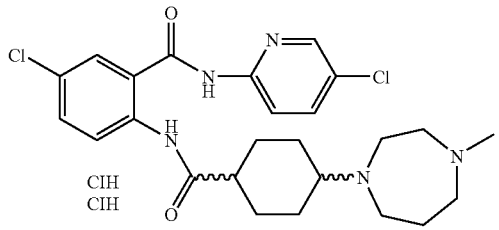

A. 5-Chloro-2-(4-oxocyclohexylcarbonylamino)-N-(5-chloropyridin-2-yl)benzamide.

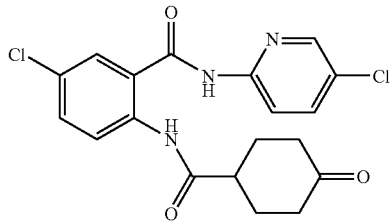

To a mixture of 4-oxocyclohexanoic acid (1 g, 7.03 mmol), $CH_2Cl_2$ (25 ml), DMF (0.016 mL, 0.211 mmol), and pyridine (0.58 ml, 7.25 mmol) at 0° C. was added oxalyl chloride (0.62 mL, 7.11 mmol); The reaction mixture was allowed to warm to room temperature and stirred for 1.5 h. This mixture was added to a 0° C. mixture of 2-amino-5-chloro-N-(5-chloropyridin-2-yl)benzamide (2.0 g, 7.03 mmol), pyridine (0.85 mL, 10.6 mmol), and $CH_2Cl_2$ (25 mL). The reaction mixture was allowed to warm to room temperature and stirred overnight. The mixture was filtered and the filtrate was concentrated and chromatographed (125 g silica gel, $CH_2Cl_2$ to 15% EtOAc/$CH_2Cl_2$) to give the title compound as a solid (600 mg, 21%).

¹NMR (300 MHz, DMSO-d₆): δ 1.82(m, 2H), 2.08(m, 2H), 2.27(m, 2H), 2.39(m, 2H), 2.81(m, 1H), 7.58(dd, J=2.6, 8.8 Hz, 1H), 7.77(d, J=2.6 Hz, 1H), 7.94(d, J=8.8 Hz, 1H), 7.96(dd, J=2.6, 8.8 Hz, 1H), 8.14(d, J=8.8 Hz, 1H), 8.43(d, J=2.6 Hz, 1H), 10.33(s, 1H), 11.10(s, 1H). FIA-MS, m/e 406.4 (M+1).

B. 5-Chloro-2-[4-(4-methylhexahydro-1,4-diazepin-1-yl)-cyclohexylcarbonylamino]-N-(5-chloropyridin-2-yl)benzamide Dihydrochloride.

To a mixture of 5-chloro-2-[4-oxocyclohexylcarbonylamino]-N-(5-chloropyridin-2-yl)benzamide (600 mg, 1.5 mmol), 1-methyl-hexahydro-1,4-diazepine (0.57 mL, 4.6 mmol), methanol (30 mL) and methylene chloride (15 mL) was added NaCNBH₃ (66 mg, 1.05 mmol) and the mixture was stirred for four days. To the reaction mixture was added additional 1-methyl-hexahydro-1,4-diazapine (0.19 mL, 1.5 mmol) followed by NaCNBH₃ (22 mg, 0.35 mmol) and the mixture was stirred for 1 day. The reaction mixture was acidified with 1 N HCl, stirred for 1 h, and then concentrated in vacuo. To the residue was added methylene chloride and the resulting solution was washed with satd $Na_2CO_3$ solution. The organic layer was concentrated and chromatographed on 60 g silica gel ($CH_2Cl_2$ to 5% 2 M $NH_3$/MeOH in $CH_2Cl_2$) followed by further HPLC purification (Vydac C18; 5% $CH_3CN$/(0.1% TFA in $H_2O$) to 70% $CH_3CN$/(0.1% TFA in $H_2O$).; Rt: 20.3 min) to give the title compound as a solid (340 mg, 39%).

¹H-NMR (400 MHz, DMSO-d₆): δ 1.32–1.74(m, 4H), 1.75–2.36(m, 7H), 2.73(s, 3H), 3.05–3.87(m, 9H), 7.54(dd, J=2.4, 8.8 Hz, 1H), 7.73(d, J=8.8 Hz, 1H), 7.78–8.00(m, 2H), 8.08(m, 1H), 8.41(m, 1H), 10.27(s, 1H), 11.08(s, 1H), 11.10(br s, 1H), 11.50(br s, 1H).

FIA-MS, m/e 504.1 (m+1).

Analysis for $C_{25}H_{33}Cl_4N_5O_2 \cdot 2HCl$: Calcd: C, 52.01; H, 5.76; N, 12.13; Found: C, 52.59*; H, 5.51; N, 12.44.

EXAMPLE 24

Preparation of 2-[4-(4-Methylhexahydro-1,4-diazepin-1-yl)-piperidin-1-ylcarbonyl]amino-N-(5-chloropyridin-2-yl)-benzamide.

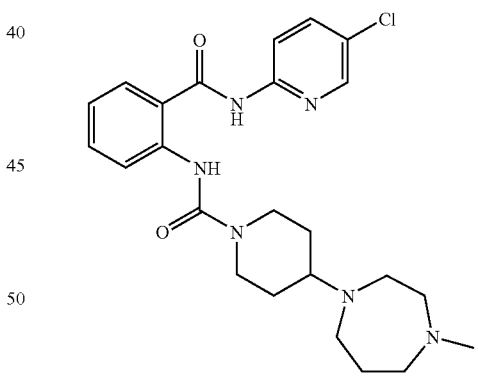

A. Methyl 2-(1,4-Dioxa-8-azaspiro[4.5]decan-8-ylcarbonyl)-aminobenzoate.

A solution of 2-carbomethoxyphenyl isocyanate (10.0 g, 56.5 mmol) in methylene chloride (300 mL) was treated with the ethylene glycol ketal of 4-piperidinone (7.93 mL, 62.1 mmol). After 17 h, the mixture was concentrated and the residue partitioned between EtOAc and 1 N HCl. The organic layer was washed with 1 N HCl (1×), 1 N NaOH (2×), brine, dried with sodium sulfate, and concentrated yielding 17.2 g of the title compound; which was used without further purification.

¹H-NMR

B. 2-(1,4-Dioxa-8-azaspiro[4.5]decan-8-ylcarbonyl)aminobenzoic Acid.

A solution of methyl 2-(1,4-dioxa-8-azaspiro[4.5]decan-8-ylcarbonyl)aminobenzoate (2.00 g, 6.25 mmol) in dioxane (30 mL) was treated with 5 N NaOH (12.5 mL). After 1 h, the mixture was poured into EtOAc and water, and the aqueous layer was washed with EtOAc. The pH of the aqueous layer was then adjusted to 2–3 by addition of 5 N HCl and washed with EtOAc (3×). The combined organic layers were washed with brine, dried with sodium sulfate, and concentrated, yielding the title compound; which was used without further purification.

¹H-NMR

IS-MS, m/e 307 (m+1)

C. 2-(1,4-Dioxa-8-azaspiro[4.5]decan-8-yl)-4H-3,1-benzoxazin-4-one.

To a stirring solution of 2-(1,4-dioxa-8-azaspiro[4.5]decan-8-ylcarbonyl)aminobenzoic acid (1.91 g, 6.25 mmol) in DMF (12 mL) was added 1-(3-dimethylaminopropyl)-3-ethylcarbodiimide hydrochloride (1.20 g, 6.25 mmol). After 30 min, the solvent was removed in vacuo and the residue was partitioned between ethyl acetate and water. The layers were separated and the organic phase was washed consecutively with 1 M citric acid, brine, satd aq sodium bicarbonate, and brine, then dried with MgSO₄, filtered and concentrated in vacuo. The residue was then suspended in diethyl ether, sonicated, filtered and dried in vacuo to give 1.36 g of the title compound; which was used without further purification.

¹H-NMR

IS-MS, m/e 288 (M+1)

D. N-(5-Chloropyridin-2-yl)-2-(1,4-dioxa-8-azaspiro[4.5]decan-8-ylcarbonyl)aminobenzamide.

To a stirred solution of 2-amino-5-chloropyridine (573 mg, 4.51 mmol) in tetrahydrofuran (25 mL) at 0° C. under nitrogen was added methylmagnesium bromide (3.0 M in ether, 1.50 mL, 4.51 mmol) dropwise via a syringe. After stirring at 0° C. for 10 min, 2-(1,4-dioxa-8-azaspiro[4.5]decan-8-yl)-4H-3,1-benzoxazin-4-one (1.30 g, 4.51 mmol) was added. After stirring 15 h at room temperature, the solvent was removed in vacuo. The residue was partitioned between ethyl acetate and saturated aqueous sodium chloride and the layers separated. The organic phase was washed with water, dried (magnesium sulfate), filtered, and concentrated in vacuo to give, after recrystallization from EtOAc, 880 mg (47%) of the title compound.

¹H-NMR

IS-MS, m/e 417 (M+1)

Analysis for C₂₀H₂₁ClN₄O₄: Calcd: C, 57.63; H, 5.08; N, 13.44; Found: C, 58.10; H, 4.97; N, 13.78.

E. N-(5-Chloropyridin-2-yl)-2-(4-oxopiperidin-1-yl-carbonyl)aminobenzamide.

A solution of N-(5-chloropyridin-2-yl)-2-(1,4-dioxa-8-azaspiro[4.5]decan-8-ylcarbonyl)aminobenzamide (120 mg, 0.289 mmol) in dioxane (1 mL) and water (0.25 mL) was treated with 12 N HCl (0.25 mL). After 1.5 h, the mixture was poured into EtOAc and water. The organic layer was washed with satd sodium bicarbonate (2×), brine, dried with sodium sulfate, and concentrated yielding 100 mg of the title compound; which was used without further purification.

¹H-NMR

IS-MS, m/e 373 (M+1)

F. 2-[4-(4-Methylhexahydro-1,4-diazepin-1-yl)piperidin-1-ylcarbonyl]amino-N-(5-chloropyridin-2-yl)benzamide.

A solution of N-(5-chloropyridin-2-yl)-2-(4-oxo-piperidin-1-ylcarbonyl)aminobenzamide (100 mg, 0.268 mmol) and 4-methyl(hexahydro-1,4-diazepine) (0.03 mL, 0.241 mmol) in 10% acetic acid in methanol (2.2 mL) was treated with sodium cyanoborohydride (20 mg, 0.268 mmol). After 15 h, the mixture was loaded onto a SCX column, which was pretreated with a solution of 5% acetic acid in methanol. The column was eluted with methanol followed by 2 N ammonia in methanol. The eluent was concentrated to afford title compound.

¹H-NMR

IS-MS, m/e 471 (M+1)

EXAMPLE 25

Preparation of 5-Chloro-2-[1-(1-methylhexahydroazepin-4-yl)-piperidin-4-ylcarbonylamino]-N-(5-chloropyridin-2-yl)-benzamide.

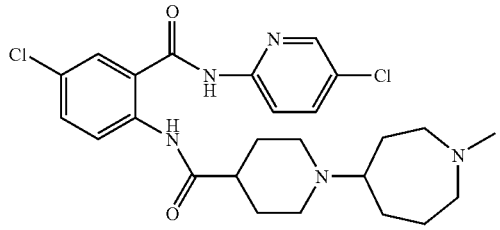

A. 1-methyl-hexahydro-4H-azepin-4-one.

4-Hydroxy-1-methylhexahydroazepine (commercially available from KOEI Chemical Co., Osaka, Japan) is oxidized using either Swern's reagent [for example, dimethyl sulfoxide and oxalyl chloride in dichloromethane, see A. J. Mancuso, D. S. Brownfain, D. Swern, *J. Org. Chem.*, (1979), 44, 4148–4150] or with Dess-Martin periodinane reagent [for example, 1,1,1-triacetoxy-2,1-benzoxidol-3 (3H)-one with trifluoroactic acid in dichloromethane, see D. B. Dess, J. C. Martin, *J. Amer. Chem. Soc.*, (1991), 113, 7277–7287].

B. 5-Chloro-2-[1-(1-methyl-hexahydroazepin-4-yl)piperidin-4-ylcarbonylamino]-N-(5-chloropyridin-2-yl)benzamide.

The title compound is prepared from 5-chloro-2-(piperidin-4-ylcarbonylamino)-N-(5-chloropyridin-2-yl)-benzamide and 1-methyl-hexahydro-4H-azepin-4-one by reductive alkylation using NaCNBH₃ and 5%-acetic acid in methanol, for example using a procedure similar to that of Example 25-F.

Alternatively, 5-chloro-2-[1-(1-methyl-hexahydroazepin-4-yl)piperidin-4-ylcarbonylamino]-N-(5-chloropyridin-2-yl)-benzamide is prepared by a NaCNBH₃ reductive alkylation of 5-chloro-2-[1-(hexahydroazepin-4-yl)piperidin-4-ylcarbonylamino]-N-(5-chloropyridin-2-yl)benzamide with formaldehyde.

5-Chloro-2-[1-(hexahydroazepin-4-yl)piperidin-4-yl-carbonylamino]-N-(5-chloropyridin-2-yl)benzamide (which itself is an example of the invention) for the above alkylation may be obtained as follows. A solution of 1-t-butoxycarbonylpiperidin-4-carboxylic acid is treated with pyridine, DMF and oxalyl chloride. The resulting acid chloride is reacted with of 2-amino-5-chloro-N-(5-chloropyridin-2-yl)

benzamide to yield 5-chloro-2-[1-(t-butoxycarbonylpiperidin-4-ylcarbonyl)amino]-N-(5-chloropyridin-2-yl) benzamide. 5-Chloro-2-[1-(t-butoxycarbonylpiperidin-4-ylcarbonyl) amino]-N-(5-chloropyridin-2-yl)benzamide is treated with TFA followed by NaCNBH$_3$ reductive alkylation with 1-(t-butoxycarbonyl)hexahydroazepin-4-one to give 5-chloro-2-[1-[1-(t-butoxycarbonyl)hexahydroazepin-4-yl]-piperidin-4-ylcarbonylamino]-N-(5-chloropyridin-2-yl)-benzamide. Treatment of 5-chloro-2-[1-[1-(t-butoxycarbonyl)hexahydroazepin-4-yl]piperidin-4-ylcarbonylamino]-N-(5-chloropyridin-2-yl)benzamide with TFA gives 5-chloro-2-[1-(hexahydroazepin-4-yl)piperidin-4-ylcarbonylamino]-N-(5-chloropyridin-2-yl)benzamide.

What is claimed is:

1. A compound of formula I,

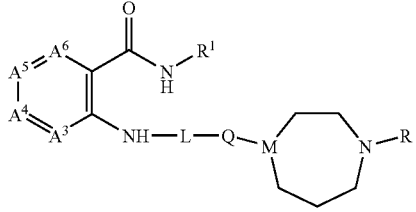

or a pharmaceutically acceptable salt thereof, wherein
R$^1$ is 2-pyridinyl (which may bear a methyl, methoxy, methylthio, fluoro or chloro substituent at the 5-position), or R$^1$ is 3-pyridinyl (which may bear a methyl, fluoro or chloro substituent at the 6-position), or R$^1$ is phenyl (which may bear one, two or three substituents at the 3-, 4- or 5-position(s) independently selected from halo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R$^1$ is 6-indolyl (which may bear a chloro or methyl substituent at the 3-position), or R$^1$ is 6-indazolyl (which may bear a methyl substituent at the 3-position);
A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$; wherein
R$^3$ is hydrogen, fluoro, chloro, methyl, methoxy, hydroxy or carboxy;
one of R$^4$ and R$^5$ is hydrogen, (1–4C)alkyl, halo, trifluoromethyl, trifluoro-methoxy, cyano, hydroxymethyl, (1–3C)acyl, R$^f$O—, R$^f$O$_2$C—, R$^f$O$_2$C—CH$_2$—, R$^f$O$_2$C—CH$^2$—O—, methylthio or R$^g$NH—;
the other of R$^4$ and R$^5$ is hydrogen, halo or methyl; and R$^6$ is hydrogen, fluoro, chloro, methyl or methoxy;
in which R$^f$ is hydrogen, (1–4C)alkyl or benzyl; R$^g$ is hydrogen, (1–3C)acyl, trifluoroacetyl, methoxyacetyl, or R$^h$SO$_h$— (wherein h is 1 or 2); and R$^h$ is (1–4C) alkyl, trifluoromethyl, phenyl, amino, methylamino or dimethylamino; or
A$^3$, A$^4$, A$^5$ and A$^6$, together with the two carbons to which they are attached, complete a substituted heteroaromatic ring in which
(a) one of A$^3$, A$^4$, A$^5$ and A$^6$ is N, and each of the others is CR$^3$, CR$^4$, CR$^5$ or CR$^6$, respectively; wherein each of R$^3$, R$^4$, R$^5$ and R$^6$ is independently hydrogen or methyl, or one of R$^3$, R$^4$, R$^5$ and R$^6$ attached to a carbon which is not bonded to an N-atom is chloro and the others are hydrogen; or
(b) two adjacent residues of A$^3$, A$^4$, A$^5$ and A$^6$ together form S, and each of the others is CR$^3$, CR$^4$, CR$^5$ or CR$^6$, respectively; wherein
each of R$^3$, R$^4$, R$^5$ and R$^6$ is hydrogen, or one or two of R$^3$, R$^4$, R$^5$ and R$^6$ is independently chloro, bromo or methyl and the others are hydrogen; or
(c) A$^3$ and A$^4$ together form a fused benz ring, and A$^5$ and A$^6$ together form —NH—;
L is carbonyl or methylene; M is N and Q (showing L and M at the points of attachment) is a residue of formula Q$^A$,

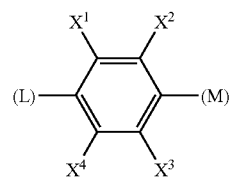

in which
each of X$^1$, X$^2$, X$^3$ and X$^4$ is hydrogen; or
X$^1$ is OR$^Q$ and each of X$^2$, X$^3$ and X$^4$ is hydrogen in which R$^Q$ is hydrogen, (1–3 C)alkyl, (3–6C)cycloalkyl, 2-hydroxyethyl, 2-methoxyethyl or 2-methylthioethyl; or
one of X$^1$ and X$^2$ is trifluoromethyl; and each of the others of X$^1$, X$^2$, X$^3$ and x$^4$ is hydrogen; or
one or two of X$^2$ and X$^3$ is fluoro; and each of the others of X$^1$, X$^2$, X$^3$ and X$^4$ is hydrogen; or
L is carbonyl or methylene; M is N; and Q is cyclohexan-1,4-diyl; or
L is carbonyl; M is N and Q is piperidin-1,4-diyl which is bonded to L at the 1-position and is bonded to M at the 4-position; and
R is hydrogen, (1–3C)alkyl, (3–5C)cycloalkyl, (1–3C) acyl, acetyloxyacetyl, aminoacetyl, hydroxyacetyl, {(1–4C)alkoxy}carbonyl, {(1–4C)alkoxy}carbonyl-methyl, R$^a$R$^b$N—CO— or R$^j$SO$_j$—, wherein each of R$^a$ and R$^b$ is independently hydrogen or (1–3C)alkyl, or R$^a$R$^b$N— is 1-azetidinyl, 1-pyrrolidinyl, 1-piperidinyl, 4-morpholinyl, or 4-thiomorpholinyl; j is 1 or 2; and R$^j$ is (1–4C)alkyl, trifluoro-methyl, amino, methylamino or dimethylamino.

2. The compound, or salt thereof, of claim 1 wherein halo is fluoro, chloro or bromo; (1–3C)alkyl is methyl, ethyl, propyl or isopropyl; (1–4C)alkyl is methyl, ethyl, propyl, isopropyl, butyl, isobutyl or t-butyl; (3–5C)cycloalkyl is cyclopropyl, cyclobutyl or cyclopentyl; (3–6C)cycloalkyl is cyclopropyl, cyclopentyl or cyclohexyl; (1–4C)alkoxy is methoxy, ethoxy, propoxy, isopropoxy, butoxy, isobutoxy or t-butoxy; and (1–3C)acyl is formyl, acetyl or propionyl.

3. The compound, or salt thereof, of claim 2 wherein
R$^1$ is 2-pyridinyl (which may bear a methyl, methoxy, methylthio, fluoro or chloro substituent at the 5-position), or R$^1$ is 3-pyridinyl (which may bear a methyl, fluoro or chloro substituent at the 6-position), or R$^1$ is phenyl (which may bear a substituent at the 3- or 4-position(s) independently selected from halo, cyano, carbamoyl, methyl, methoxy, difluoromethoxy, hydroxymethyl, formyl, vinyl, amino, hydroxy and 3,4-methylenedioxy), or $R^1$ is 6-indolyl (which may bear a chloro or methyl substituent at the 3-position); $A^3$ is $CR^3$, $A^4$ is $CR^4$, $A^5$ is $CR^5$, and $A^6$ is $CR^6$; wherein $R^3$ is hydrogen;

one of $R^4$ and $R^5$ is hydrogen, (1–4C)alkyl, halo, trifluoromethyl, trifluoro-methoxy, cyano, hydroxymethyl, (1–3C)acyl, $R^fO$—, $R^fO_2C$—, $R^fO_2C$—$CH_2$—, $R^fO_2C$—$CH_2$—O—, methylthio or $R^gNH$— in which $R^g$ is hydrogen, (1–3C)acyl, or $R^hSO_2$—; and $R^h$ is (1–4C)alkyl, trifluoromethyl, amino, methylamino or dimethylamino;

the other of $R^4$ and $R^5$ is hydrogen, halo or methyl; and $R^6$ is hydrogen; or $A^3$ is N, and each of $A^4$, $A^5$ and $A^6$ is $CR^4$, $CR^5$ and $CR^6$, respectively, in which each of $R^4$ and $R^6$ is hydrogen and $R^5$ is hydrogen, chloro or methyl; or $A^6$ is N, and each of $A^3$, $A^4$ and $A^5$ is $CR^3$, $CR^4$ and $CR^5$, respectively, in which each of $R^3$ and $R^4$ is hydrogen and $R^5$ is hydrogen or methyl; and R is hydrogen, methyl, ethyl, acetyl, acetoxyacetyl, hydroxyacetyl, methylsulfonyl or dimethylaminosulfonyl.

4. The compound, or salt thereof, of claim 3 wherein $R^1$ is 2-pyridinyl which bears a methyl or chloro substituent at the 5-position, $A^3$ is $CR^3$, $A^4$ is $CR^4$, $A^5$ is $CR^5$, and $A^6$ is $CR^6$ wherein each of $R^3$, $R^4$ and $R^6$ is hydrogen and $R^5$ is fluoro, chloro or methyl; or $A^3$ is N, and each of $A^4$, $A^5$ and $A^6$ is CH; or $A^6$ is N, and each of $A^3$, $A^4$ and $A^5$ is CH; and R is hydrogen or methyl.

5. The compound, or salt thereof, of any one of claims 1–4 wherein Q is QA in which each of $X^1$, $X^2$, $X^3$ and $X^4$ is hydrogen; or $X^1$ is $OR^Q$ and each of $X^2$, $X^3$ and $X^4$ is hydrogen in which $R^Q$ is hydrogen, (1–3C)alkyl, (3–6C)cycloalkyl, 2-methoxyethyl or 2-methylthioethyl; or $X^1$ is trifluoromethyl and each of $X^2$, $X^3$ and $X^4$ is hydrogen; or $X^2$ is trifluoromethyl and each of $X^1$, $X^3$ and $X^4$ is hydrogen; or $X^2$ is fluoro and each of $X^1$, $X^3$ and $X^4$ is hydrogen; or each of $X^2$ and $X^3$ is fluoro and each of $X^4$ and $X^4$ is hydrogen.

6. The compound, or salt thereof, of claim 5 wherein each of $X^1$, $X^2$, $X^3$ and $X^4$ is hydrogen.

7. The compound, or salt thereof, of claim 5 wherein $X^1$ is $OR^Q$ and each of $X^2$, $X^3$ and $X^4$ is hydrogen in which $R^Q$ is hydrogen, ethyl, isopropyl, 2-methoxyethyl or 2-methylthioethyl.

8. The compound, or salt thereof, of claim 5 wherein $X^1$ is trifluoromethyl and each of $X^2$, $X^3$ and $X^4$ is hydrogen.

9. The compound, or salt thereof, of claim 5 wherein $X^2$ is trifluoromethyl and each of $X^1$, $X^3$ and $X^4$ is hydrogen.

10. The compound, or salt thereof, of claim 5 wherein $X^2$ is fluoro and each of $X^1$, $X^3$ and $X^4$ is hydrogen.

11. The compound, or salt thereof, of claim 5 wherein each of $X^2$ and $X^3$ is fluoro and each of $X^1$ and $X^4$ is hydrogen.

12. The compound, or salt thereof, of any one of claims 1–4 wherein Q is cyclohexan-1,4-diyl.

13. The compound, or salt thereof, of any one of claims 1–4 wherein L is carbonyl.

14. The compound, or salt thereof, of any one of claims 1–4 wherein L is methylene.

15. The compound, or salt thereof, of any one of claims 1–4 wherein Q is piperidin-1,4-diyl which is bonded to L at the 1-position and is bonded to M at the 4-position.

16. The compound of claim 1 which is selected from a. 5-fluoro-2-[4-(4-methylhexahydro-1,4-diazepin-1-yl) benzoylamino]-N-(5-chloropyridin-2-yl)benzamide, b. 3-[4-(4-methylhexahydro-1,4-diazepin-1-yl)benzoylamino]-N-(5-chloro-pyridin-2-yl)pyridine-2-carboxamide, c. 5-fluoro-2–4-(4-methylhexahydro-1,4-diazepin-1-yl)-2-trifluoromethyl-benzoylamino]-N-(5-chloropyridin-2-yl)benzamide, d. 5-chloro-2-[4-(4-methylhexahydro-1,4-diazepin-1-yl)-2-trifluoromethyl-benzoylamino]-N-(5-chloropyridin-2-yl)benzamide, e. 2-[2-ethoxy-4-(4-methylhexahydro-1,4-diazepin-1-yl) benzoylamino]-5-fluoro-N-(5-chloropyridin-2-yl)benzamide, f. 5-fluoro-2-[2-isopropoxy-4-(4-methylhexahydro-1,4-diazepin-1-yl)benzoyl-amino]-N-(5-chloropyridin-2-yl)benzamide, and g. 5-fluoro-2-[2-(2-methoxyethoxy)-4-(4-methylhexahydro-1,4-diazepin-1-yl)-benzoylamino]-N-(5-chloropyridin-2-yl)-benzamide;

or a pharmaceutically acceptable salt thereof.

17. The pharmaceutically acceptable salt of claim 1 which is the acid addition salt of a basic compound of formula 1 with an inorganic or organic acid which affords a physiologically acceptable anion or which is the salt formed by an acidic compound of formula I with a base which affords a physiologically acceptable cation.

18. A process for preparing a compound of formula I, or a pharmaceutically acceptable salt thereof, as provided in claim 1, wherein a functional group of a starting material which is not involved in the indicated process may be in a form in which the functional group is protected using a protecting group, which comprises:

(A) for a compound of formula I in which Q is $Q^A$, substituting the group $Y^a$ of a compound of formula II,

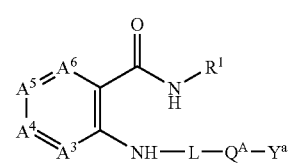

II in which $Y^a$ is a leaving group for nucleophilic aromatic substitution, using an amine of formula III,

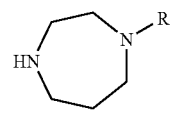

III (B) for a compound of formula I in which L is carbonyl, acylating an amine of formula IV

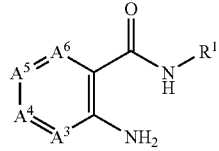

IV using a corresponding acid of formula V,

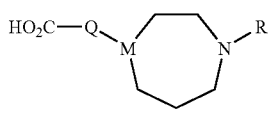

V or an activated derivative thereof;

(C) for a compound of formula I in which R is not hydrogen, substituting the nitrogen of a corresponding compound in which R is hydrogen using a conventional procedure;

(D) for a compound of formula I in which L is methylene, substituting the group $Y^a$ of a compound of formula VI

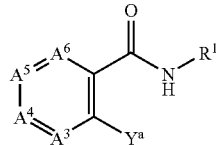

VI in which $Y^a$ is a leaving group for nucleophilic aromatic substitution with an amine of formula VII; or

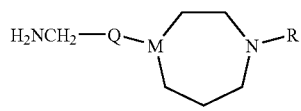

VII alkylating an amine of formula IV directly, using a compound of formula VIII,

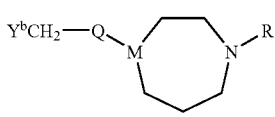

VIII in which $Y^b$ is a leaving group for nucleophilic substitution, or indirectly by reductive alkylation using an aldehyde of formula IX;

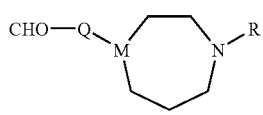

IX (E) acylating an amine of formula $H_2N-R^1$, or a deprotonated derivative thereof, using an acid of formula X,

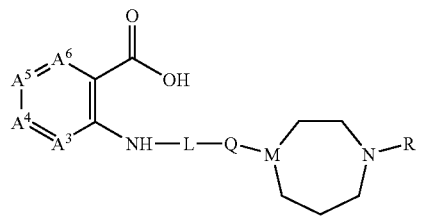

X or an activated derivative thereof; or (F) for a compound of formula I in which Q is cyclohexan-1,4-diyl or Q is piperidin-1,4-diyl which is bonded to L at the 1-position, reductively alkylating an amine of formula III using a compound of formula XIa or XIb, respectively;

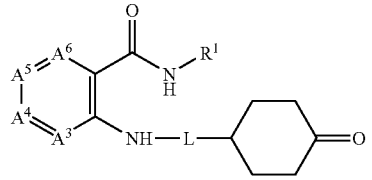

XIa

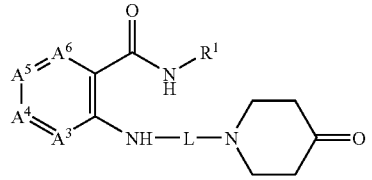

XIb whereafter, for any of the above procedures, when a functional group of a starting material is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $R^1$, $A^3$–$A^6$, L, M, Q, and R have any of the values defined in claim 1.

19. A method of treating a thromboembolic disorder in a mammal wherein the disorder is venous thrombosis, pulmonary embolism or arterial thrombosis comprising administering to a mammal in need of treatment an effective (thromboembolic disorder therapeutic and/or prophylactic amount) dose of a compound of formula I (or salt) as described in claim 1.

20. A method of inhibiting coagulation in a mammal comprising administering to a mammal in need of treatment an effective (coagulation inhibiting) dose of a compound of formula I (or salt) as described in claim 1.

* * * * *